(12) United States Patent
Setchell et al.

(10) Patent No.: US 7,960,573 B2
(45) Date of Patent: Jun. 14, 2011

(54) METHOD FOR ENANTIOSELECTIVE HYDROGENATION OF CHROMENES

(75) Inventors: Kenneth David Reginald Setchell, Cincinnati, OH (US); Victor Dmitrievich Sorokin, Cincinnati, OH (US)

(73) Assignees: Children's Hospital Medical Center, Cincinnati, OH (US); Girindus America, Inc., Cincinnati, OH (US)

( * ) Notice: Subject to any disclaimer, the term of this patent is extended or adjusted under 35 U.S.C. 154(b) by 0 days.

(21) Appl. No.: 12/435,033

(22) Filed: May 4, 2009

(65) Prior Publication Data

US 2010/0069653 A1    Mar. 18, 2010

Related U.S. Application Data

(63) Continuation of application No. 11/194,280, filed on Aug. 1, 2005, now Pat. No. 7,528,267.

(51) Int. Cl.
*C07D 311/00* (2006.01)
(52) U.S. Cl. ........ 549/399; 549/400; 549/401; 549/402; 549/403; 549/404; 549/405; 549/406
(58) Field of Classification Search .................. 549/399, 549/400, 401, 402, 403, 404, 405, 40
See application file for complete search history.

(56) References Cited

U.S. PATENT DOCUMENTS

| | | |
|---|---|---|
| 4,264,509 A | 4/1981 | Zilliken |
| 4,814,346 A | 3/1989 | Albert et al. |
| 5,922,914 A | 7/1999 | Gage et al. |
| 6,222,072 B1 | 4/2001 | Mukaiyama et al. |
| 6,310,248 B2 | 10/2001 | Andersson et al. |
| 6,576,772 B1 | 6/2003 | Zhang |
| 6,632,954 B2 | 10/2003 | Pfaltz et al. |
| 6,649,648 B1 | 11/2003 | Kelly et al. |
| 6,812,353 B2 | 11/2004 | Bokel et al. |

FOREIGN PATENT DOCUMENTS

| | | |
|---|---|---|
| EP | 267155 | 10/1987 |
| WO | WO 98/08503 | 3/1998 |
| WO | WO 00/49009 | 8/2000 |
| WO | WO 2004/039793 A1 | 5/2004 |
| WO | WO 2005/005356 A2 | 1/2005 |

OTHER PUBLICATIONS

Blackmond, DG et al., Enantioselective Hydrogenation of Olefins with Phosphinooxazoline-iridium Catalysts, Chirality Jun. 2002, 12(5-6), pp. 442-449.
Blankenstein, Jörg et al., A New Class of Modular Phosphinite-Oxazoline Ligands: Ir-Catyzed Enantioselective Hydrogenation of Alkenes, Angew. Chem, Int. Ed. 2001, (40(23), pp. 4445-4447.
Cozzi, Pier Giorgio et al., Iridium-hetPHOX Complexes for the Catalytic Asymmetric Hydrogenation of Olefins and Imines, Synlett May 5, 2003, No. 6, pp. 833-836.
Cozzi, Pier Giorgio et al., Chiral Phosphinopyrrolyl-Oxazolines: A New Class of Easily Prepared, Modular P,N-Ligands, Adv. Synth. Catal. 2001, 343(5), pp. 450-454.
Fan, Yubo et al., Electronic Effects Steer the Mechanism of Asymmetric Hydrogenations of Unfunctionalized Aryl-substituted Alkenes, J Am Chem Soc. 2004; 125(51), pp. 16688-16689.
Mazet, C. et al., A Combined Experimental and Computational Study of Dihydrido(Phosphinooxazoline)iridium Complexes, J Am Chem Soc. Nov. 3, 2004, 126(43), pp. 14174-14181.
Perry, Marc C. et al., Optically Active Iridium Imidazol-2-ylidene-oxazoline Complexes: Preparation and Use in Asymmetric Hydrogenation of Arylalkenes, J Am Chem Soc. 2003, 125(1), pp. 113-123.
Schmidt, SP et al., Enantioselective Hydrogenation of Alkenes with Iridium-PHOX Catalysts: a Kinetic Study of Anion Effects, Chemistry Oct. 4, 2004, 10(19), pp. 4685-4693.
Bunlaksananusorn, T., et al., New P,N Ligands for Asymmetric Ir-Catalyzed Reactions, Angew. Chem. Int. Ed. 2003, 42, pp. 3941-3943.
Colacot, T .J., A Concise Update on the Applications of Chiral Ferrocenyl Phosphines in Homogeneous Catalysis Leading to Organic Synthesis, Chem. Rev. 2003, 103, pp. 3101-3118.
Liu, D., et al., Synthesis of a New Class of Conformationally Rigid Phosphino-Oxazolines: Highly Enantioselective Ligands for Ir-Catalyzed Asymmetric Hydrogenation, Organic Letters, 2004, vol. 6, No. 4, pp. 513-516.
Menges, F., et al, Threonine-Derived Phosphinite-Oxazoline Ligands for the Ir-Catalyzed Enantioselective Hydrogenation, Adv. Synth. Catal. 2002, 344, No. 1, pp. 40-44.
Menges, F., et al., Synthesis and Application of Chiral Phosphino-Imidazoline Ligands: Ir-Catalyzed Enantioselective Hydrogenation, Organic Letters, 2002, vol. 4, No. 26, pp. 4713-4716.
Noyori, R. et al., Asymmetric Catalysis by Architectural and Functional Molecular Engineering: Practical Chemo-and Stereoselective Hydrogenation of Ketones, Angew Chem. Int. Ed. 2001 40, 40-73.
Ohkuma, T., et al., Asymmetric Hydrogenation of 2-Arylated Cycloalkanones through Dynamic Kinetic Resolution, Synlett 2004, No. 8, pp. 1383-1386.
Ohkuma, T., et al., BINAP/I, 4-Diamine-Ruthenium(II) Complexes for Efficient Asymmetric Hydrogenation of 1-Tetralones and Analogues, Organic Letters, 2004, vol. 6, No. 16, pp. 2681-2683.
Pfaltz, A., et al., Iridium-Catalyzed Enantioselective Hydrogenation of Olefins, Adv. Synth. Catal. 2003, 345, pp. 33-43.
Powell, M. T., et al., Chiral imidazolylidine Ligands for Asymmetric Hydrogenation of Aryl Alkenes, J. Am. Chem. Soc. 2001, 123, pp. 8878-8879.
Schenkel, L. B., et al., Application of P,N-Sulfinyl lmine Ligands to Iridium-Catalyzed Asymmetric Hydrogenation of Olefins, J. Org. Chem. 2004, 69, 1800-1802.
Smidt, S. P., et al., SimplePHOX, a Readily Available Chiral Ligand System for Iridium-Catalyzed Asymmetric Hydrogenation, Organic Letters, 2004, vol. 6, No. 12, pp. 2023-2026.
Tang, W., et al., Phospholane-Oxazoline Ligands for Ir-Catalyzed Asymmetric Hydrogenation, Angew. Chem. Int. Ed. 2003, 42, No. 8, pp. 943-943.
Xu, G., et al., Asymmetric hydrogenation of aromatic olefins catalyzed by iridium complexes of proline derived phosphine-oxazoline ligands, Tetrahedron Letters 44 (2003) 953-955.

*Primary Examiner* — Janet L. Andres
*Assistant Examiner* — Raymond Covington
(74) *Attorney, Agent, or Firm* — Rothwell, Figg, Ernst & Manbeck pc

(57) ABSTRACT

A method for preparing an enantiomeric chromane, by asymmetrically hydrogenating a chromene compound in the presence of an Ir catalyst having a chiral ligand. The method includes the enantioselective preparation of enantiomeric equol. A preferred Ir catalyst has a chiral phosphineoxazoline ligand. Enantiomeric chromanes of high stereoselective purity can be obtained.

34 Claims, 18 Drawing Sheets

GC Trace - bis-MOM Daidzein

Spectrum - bis-MOM Daidzein

LC Trace - bis-MOM Daidzein    FIG. 1C
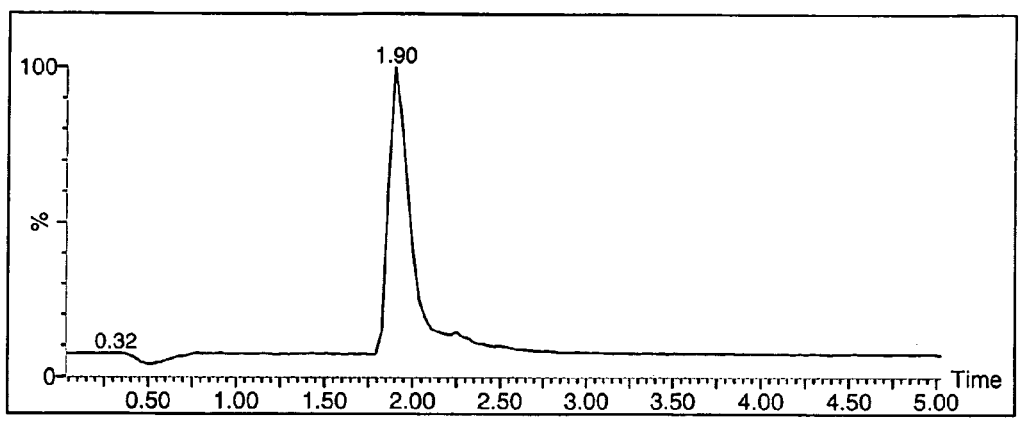
Spectrum - bis-MOM Daidzein    FIG. 1D
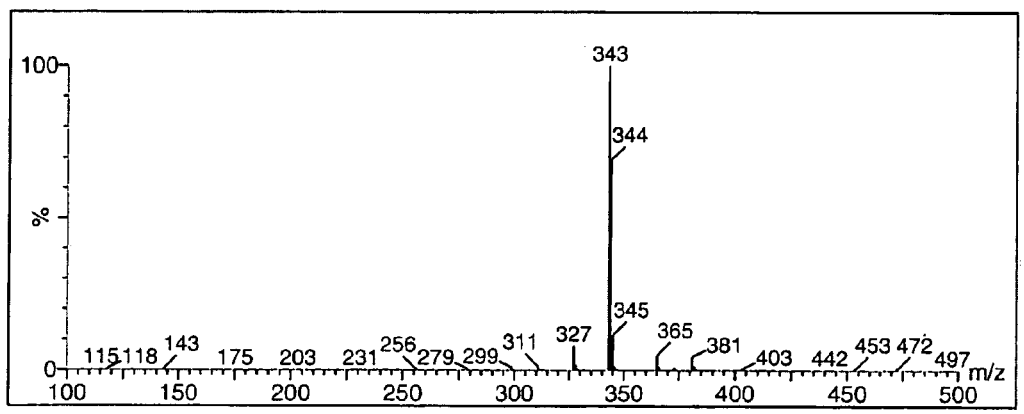

GC Trace - chroman-4-one  FIG. 2A
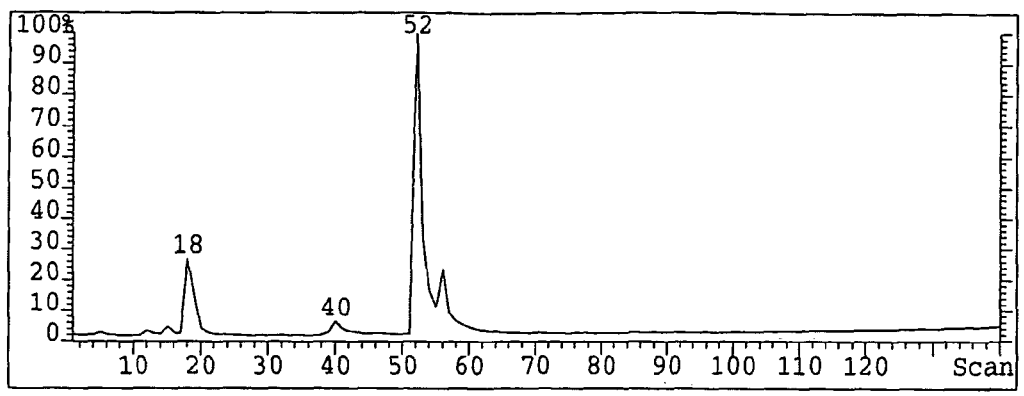
Spectrum - chroman-4-one  FIG. 2B
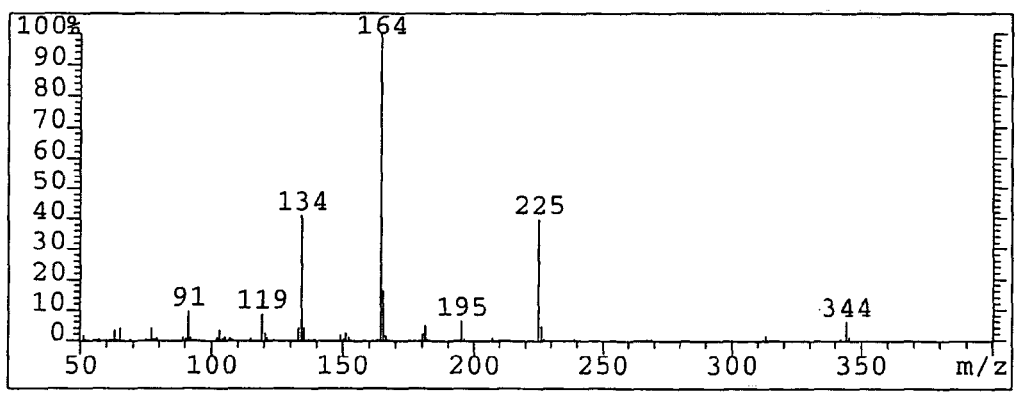

LC Trace - chroman-4-one    FIG. 2C
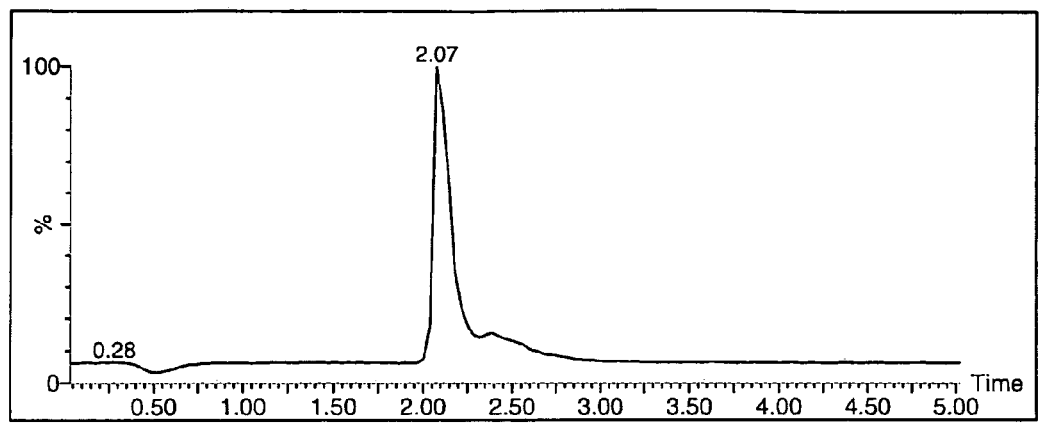
Spectrum - chroman-4-one    FIG. 2D
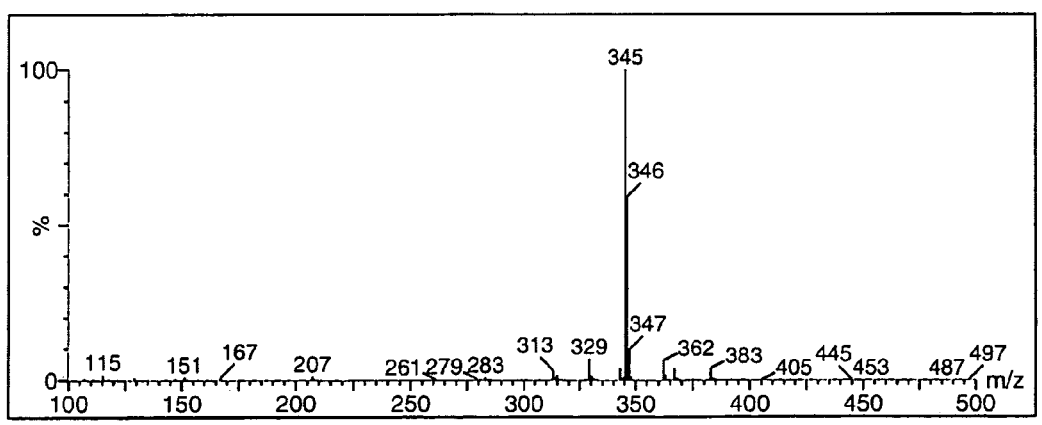

GC Trace - chroman-ol  FIG. 3A
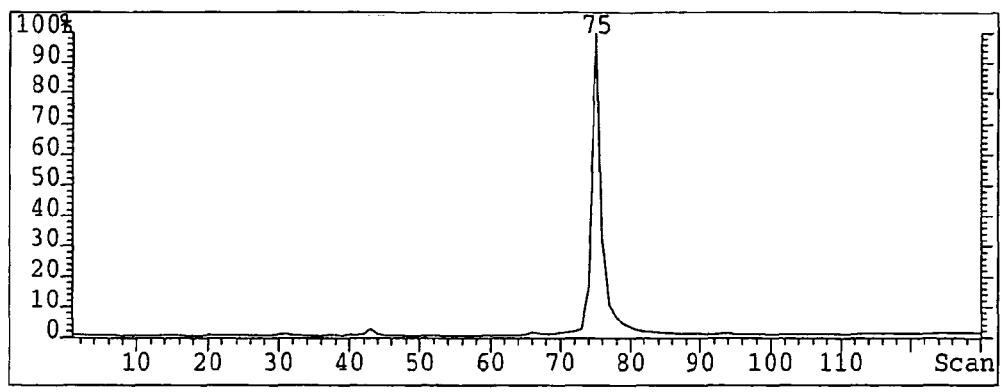
Spectrum - chroman-ol  FIG. 3B
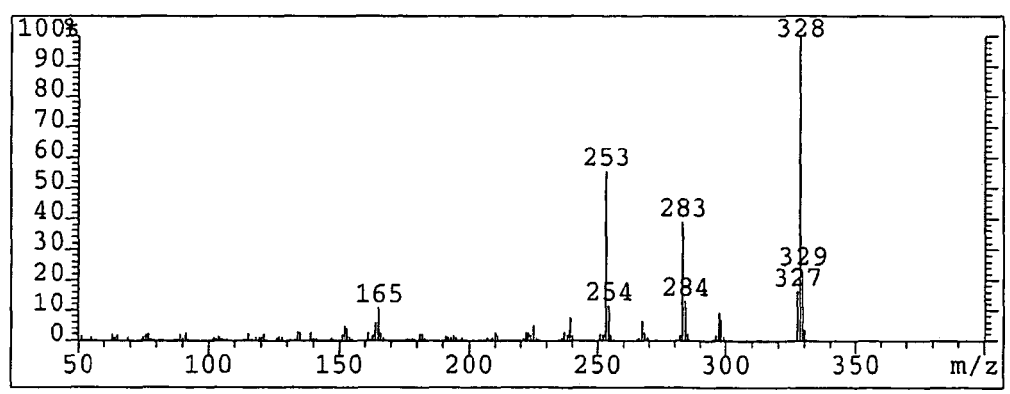

LC Trace - chroman-ol

Spectrum - chroman-ol

GC Trace - bis-MOM-dehydroequol        FIG. 4A
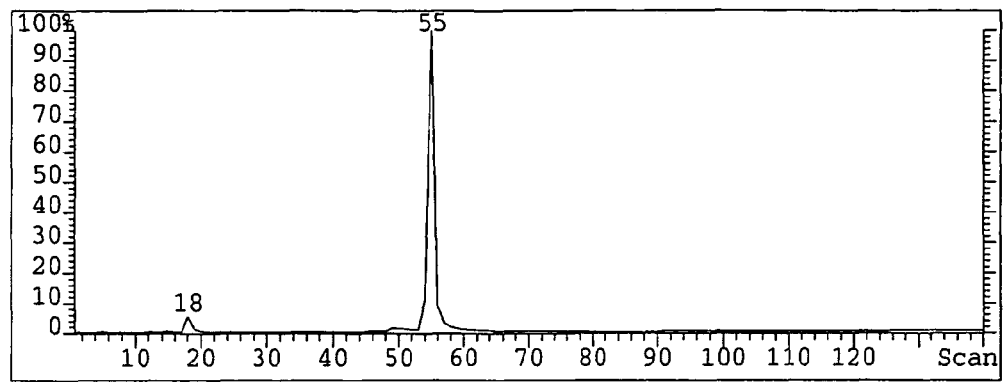
Spectrum - bis-MOM-dehydroequol        FIG. 4B
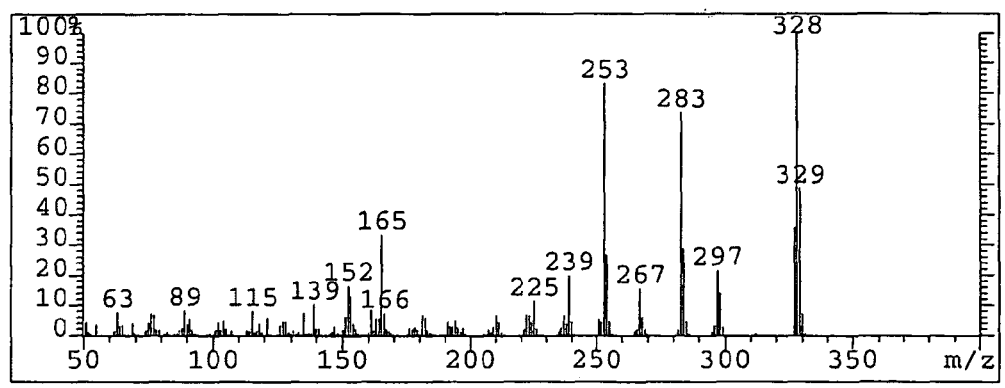

LC Trace - bis-MOM-dehydroequol  FIG. 4C
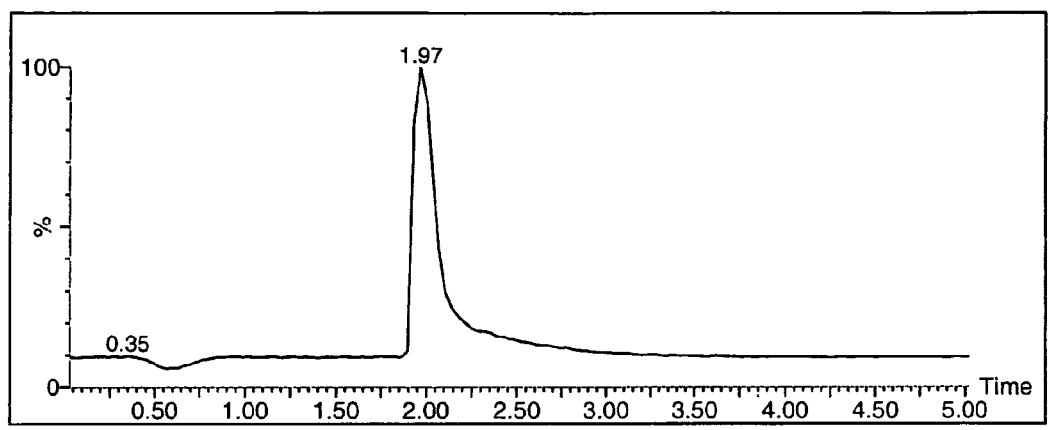
Spectrum - bis-MOM-dehydroequol  FIG. 4D
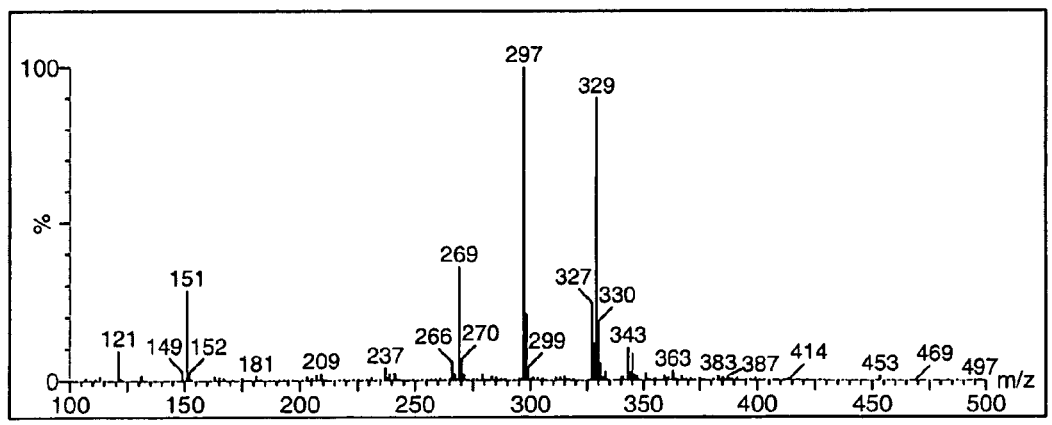

GC Trace - MOM-protected S-equol      FIG. 5A
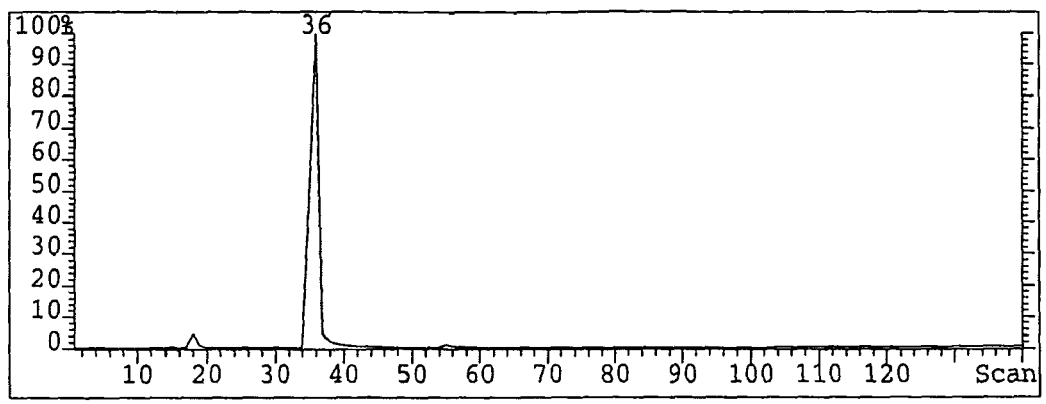
Spectrum - MOM-protected S-equol      FIG. 5B
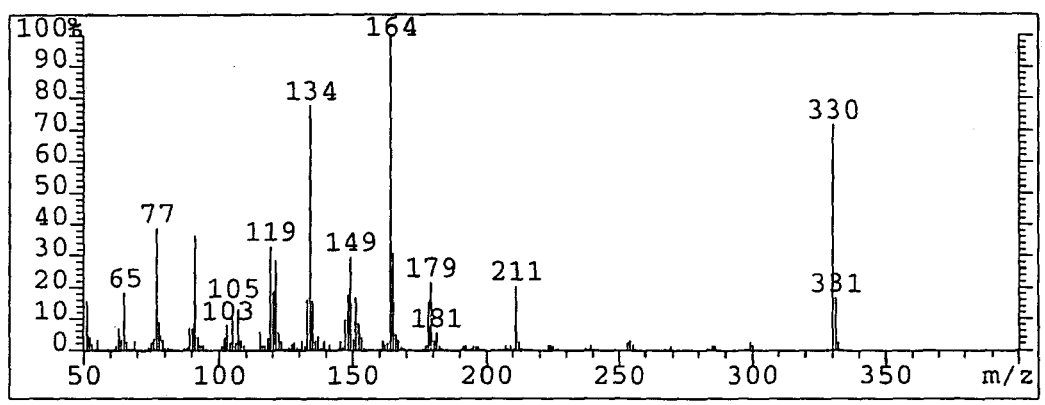

LC Trace - MOM-protected S-equol  FIG. 5C
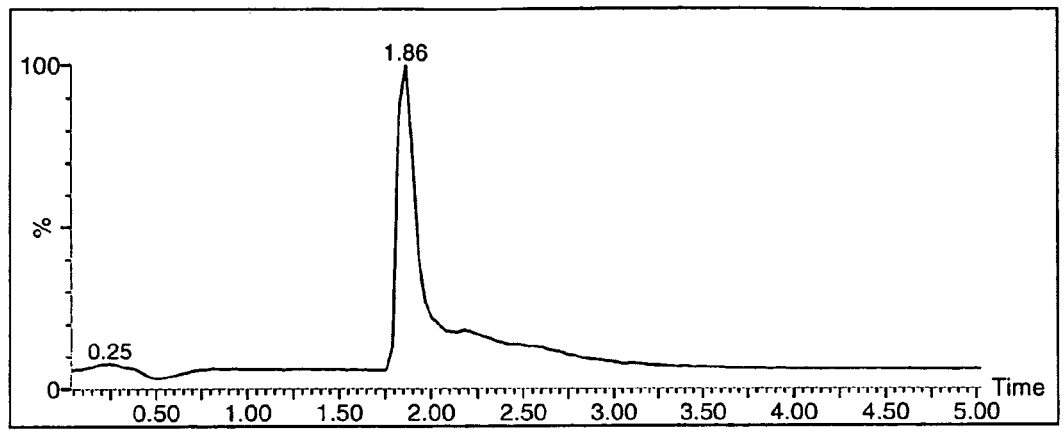
Spectrum - MOM-protected S-equol  FIG. 5D
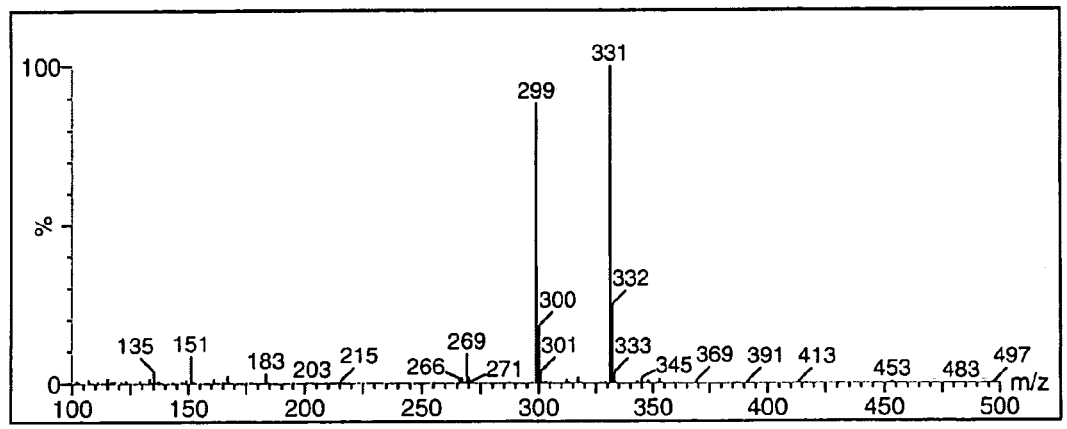

LC Trace - S-Equol  FIG. 6A
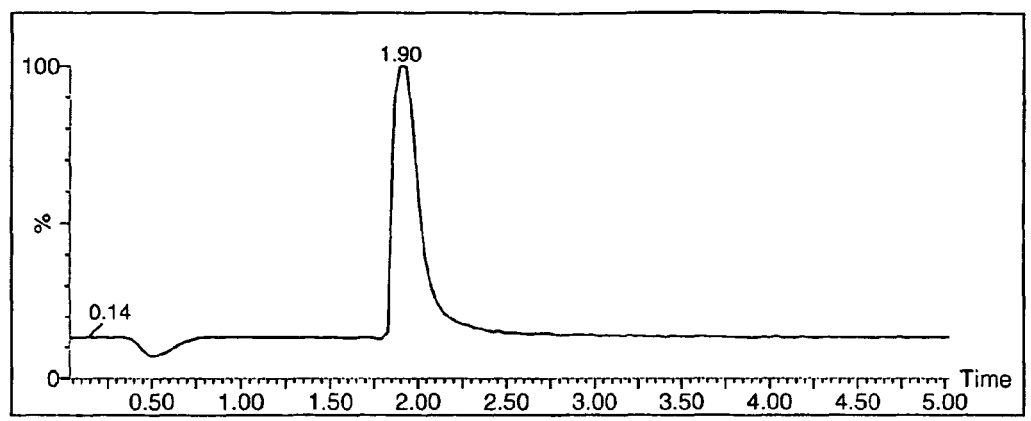
Spectrum - S-Equol  FIG. 6B
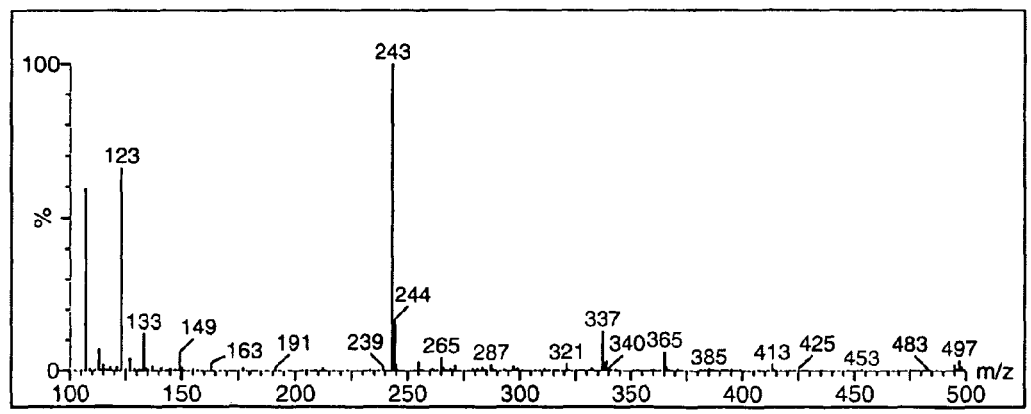

GC Trace - MOM-protected R-equol    FIG. 7A
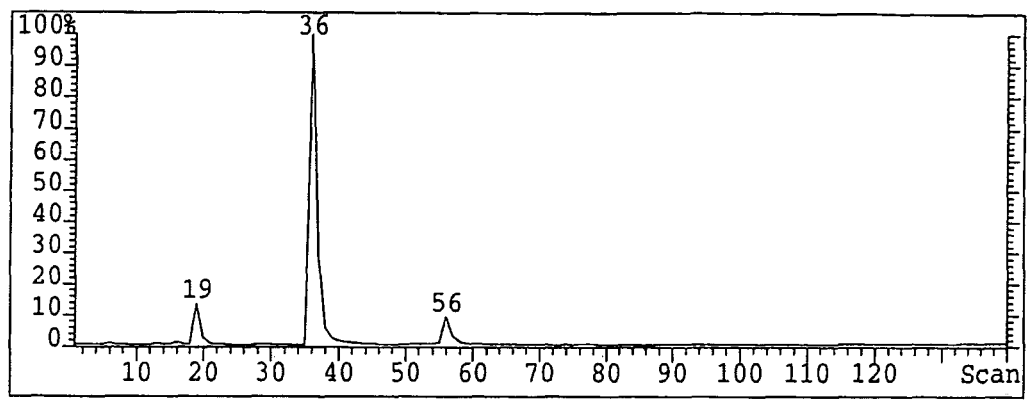
Spectrum - MOM-protected R-equol    FIG. 7B
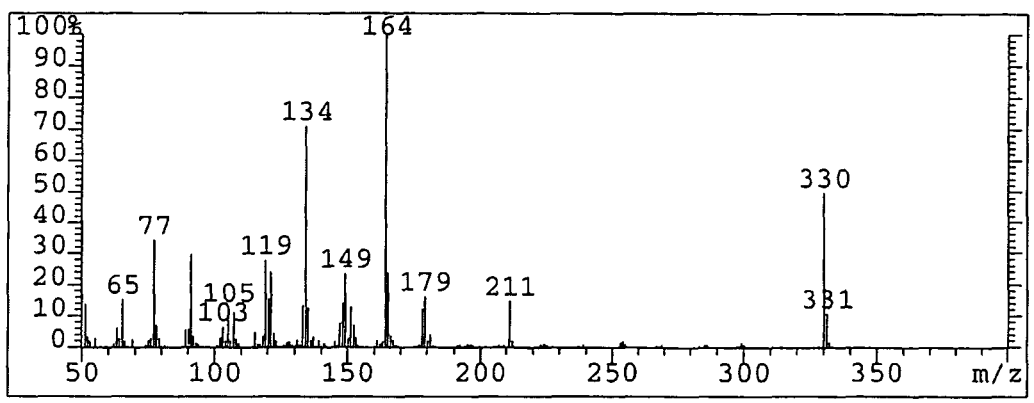

LC Trace - MOM-protected R-equol

Spectrum - MOM-protected R-equol

LC Trace - R-Equol

Spectrum - R-Equol

GC Trace - S Equol - TMS Derivative  FIG. 9A
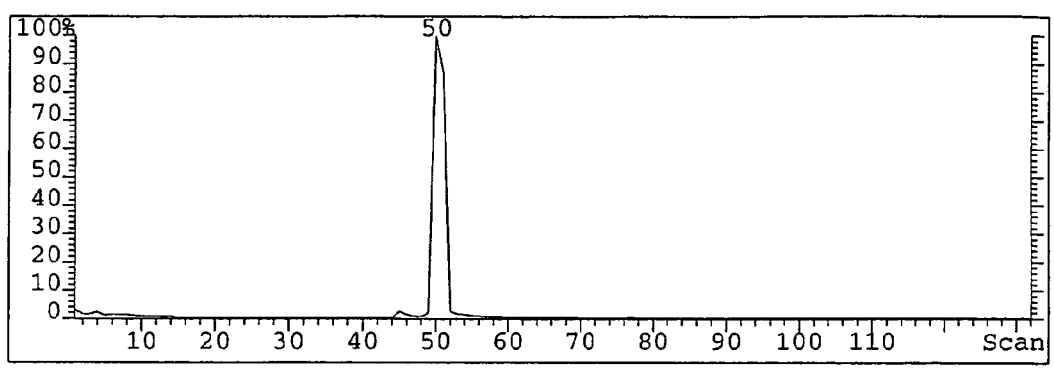
Spectrum - S Equol - TMS Derivative  FIG. 9B
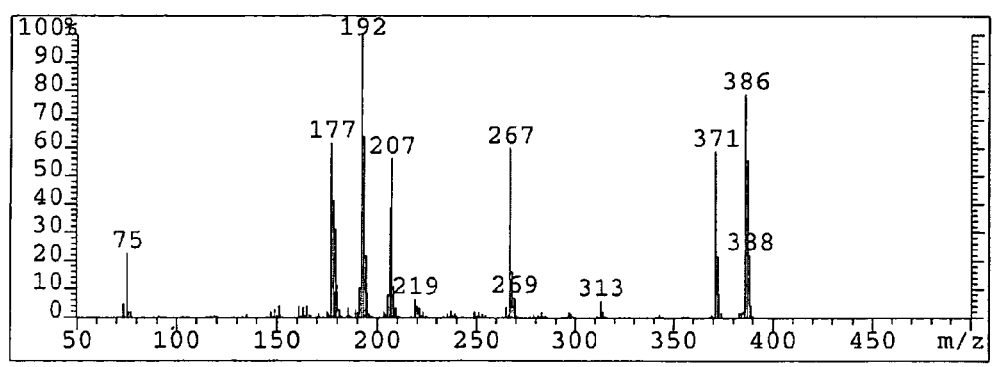

GC Trace - S Equol - TBDMS Derivative  FIG. 9C
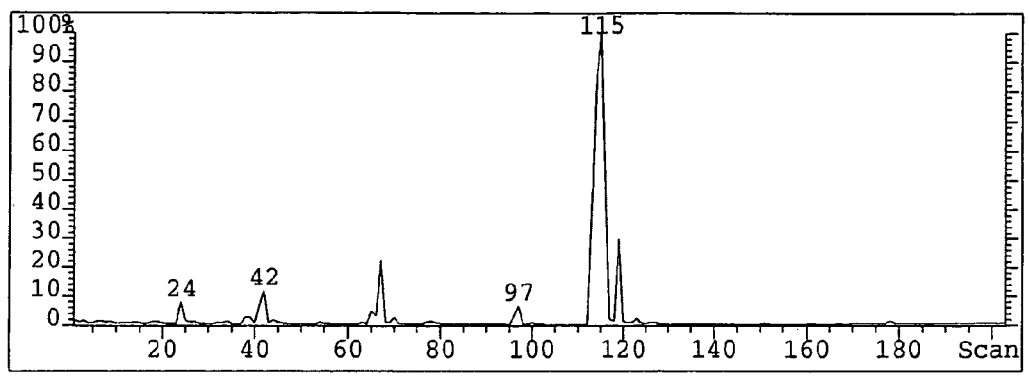
Spectrum - S Equol - TBDMS Derivative  FIG. 9D
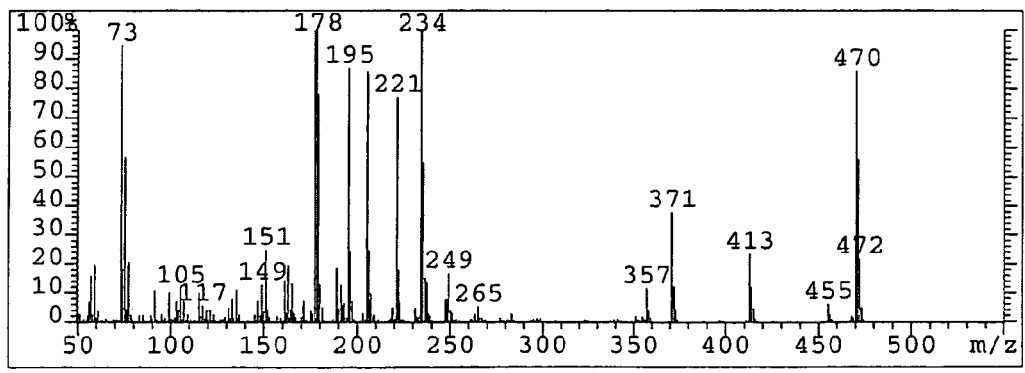

GC Trace - R Equol - TMS Derivative  FIG. 10A
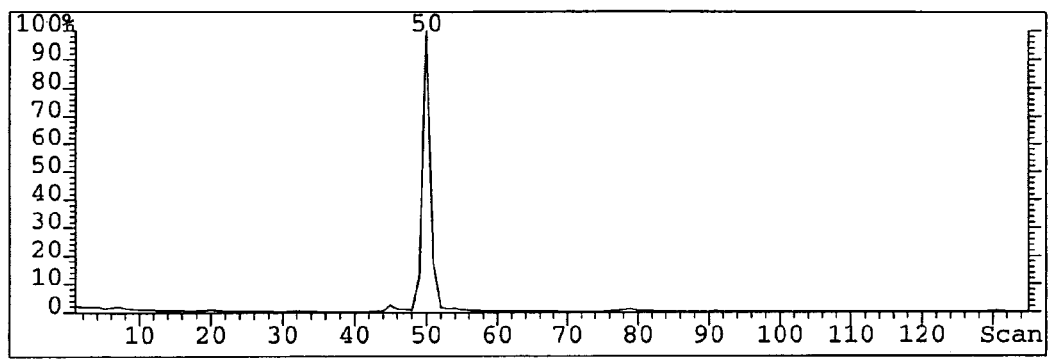
Spectrum - R Equol - TMS Derivative  FIG. 10B
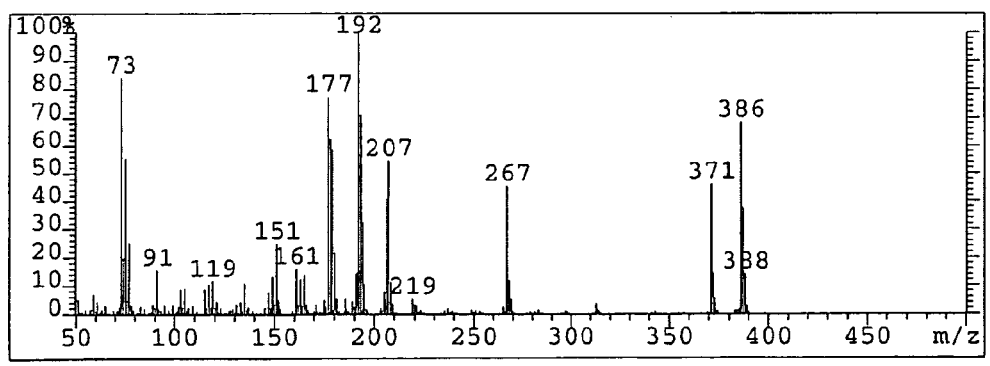

GC Trace - R Equol - TBDMS Derivative    FIG. 10C
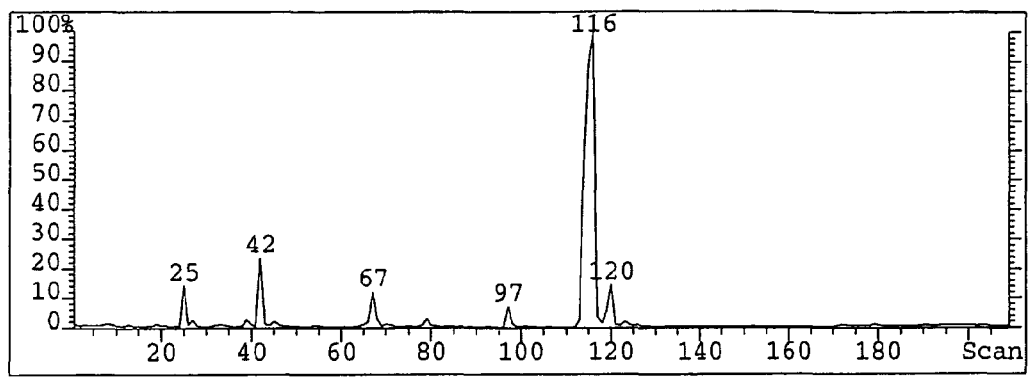
Spectrum - R Equol - TBDMS Derivative    FIG. 10D
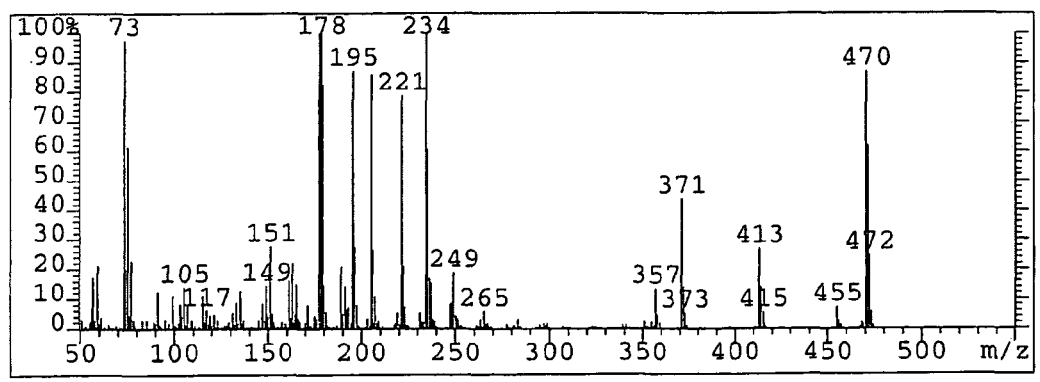

METHOD FOR ENANTIOSELECTIVE HYDROGENATION OF CHROMENES

CROSS-REFERENCE TO RELATED APPLICATIONS

This application is a continuation of U.S. application Ser. No. 11/194,280, filed Aug. 1, 2005, the disclosure of which is hereby incorporated by reference in its entirety.

BACKGROUND OF THE INVENTION

Isoflavones and many derivatives thereof possess a wide range of important biological properties including estrogenic effects. Isoflavanoids found in soy, such as genistein and daidzein, have also attracted interest as dietary phytoestrogens that might be effective for the treatment of hormone-dependent conditions and diseases. In examining the impact of the estrogenic activity of soy isoflavones (commonly referred to as phytoestrogens), one needs to consider not only the isoflavones and their conjugates that are ingested, but also biologically active metabolites that might be generated from them in vivo. Daidzein, an isoflavone in soy, can be converted to the corresponding chromane S-(−)equol, a compound with greater estrogenic activity than its precursor (See K. D. R. Setchell, N. M. Brown, E. Lydeking-Olsen. J. Nutrition, 2002, 132/12, pp 3577-3584). This reductive metabolic conversion is the result of the action of equol-producing gut microflora found in a proportion of the human population who are known as "equol producers". Equol was first isolated from pregnant mare's urine in 1932 and was subsequently identified in the plasma of sheep (derived from formononetin found in red clover species). In 1982 it was first identified in human urine. Equol is a chiral center and therefore can exist in two enantiomeric forms. It has been recently established that S-(−)equol is the enantiomer produced by the metabolic reduction of isoflavones ingested by humans (see Setchell K D R, Clerici C, Lephart E D, Cole S J, Heenan C, Castellani D, Wolfe B, Nechemias L-Z, Brown N, Baraldi G, Lund T D, Handa R J, Heubi J E. S-Equol, a potent ligand for estrogen receptor-beta, is the exclusive enantiomeric form of the soy isoflavone metabolite produced by intestinal bacterial flora. *American Journal of Clinical Nutrition* 2005; 81:1072-1079.

A convenient preparation of racemic (+) equol (7-hydroxy-3-(4'-hydroxyphenyl)-chroman) based on transfer hydrogenation of daidzein was published (K. Wahala, J. K. Koskimies, M. Mesilaakso, A. K. Salakka, T. K. Leino, H. Adlercreutz. J. Org. Chem., 1997, v 62, p 7690-7693), and more recently by J. A. Katzenellenbogen et al. (Bioorganic & Medicinal Chem., 2004, 12, pp 1559-1567). A procedure is known for isolation of enantiomeric S- and R-equol from the racemic mixture by chiral chromatographic resolution of (+) equol using a β-cyclodextrin column (see PCT Publication WO03/23056, published Jan. 29, 2004, and incorporated herein by reference). However, this approach has certain production rate limitations, and may not be suitable for making commercial quantities of enantioselective equol.

Therefore, a need remains to develop a cost-effective method of synthesizing commercial quantities of enantioselective equol and related enantioselective chromanes.

SUMMARY OF THE INVENTION

The present invention relates to a method for synthesizing enantioselective equol in high purity and yield. The invention is achieved by enantioselective hydrogenation of non-functionalized cyclic olefins, and in particular, chromenes.

The present invention also relates to a method for preparing enantioselectively an enantiomeric chromane (compound (I)):

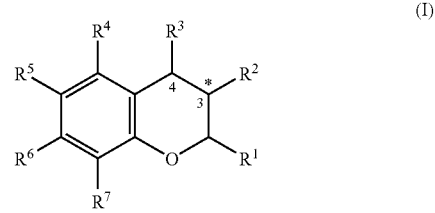

wherein each $R^4$, $R^5$, $R^6$, and $R^7$ is independently selected from the group consisting of H, OH, phenyl, aryl, alkyl, alkylaryl, arylalkyl, $OR^8$, $OC(O)R^8$, $OS(O)R^8$, thio, alkylthio, mercaptal, alkylmercaptal, amino, alkylamino, dialkylamino, nitro and halo, and where $R^8$ is alkyl and alkylaryl; and $R^1$, R2, and $R^3$ is independently selected from —$R^4$ and

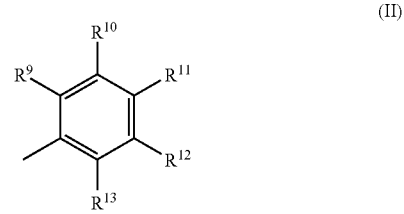

wherein each $R^9$, $R^{10}$, $R^{11}$, $R^{12}$, and $R^{13}$ is independently selected from H and $R^4$; comprising the steps of:

1) providing a chromene compound selected from:

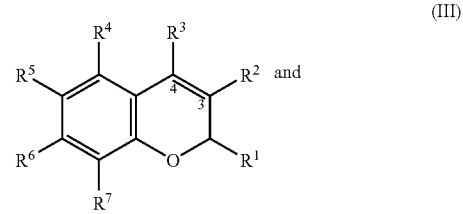

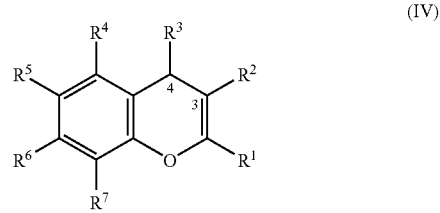

2) hydrogenating the chromene in the presence of an Ir catalyst having a chiral ligand shown as compound (V):

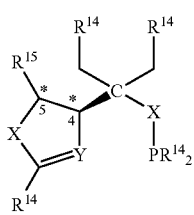

(V)

to form the chromane; wherein each of Y and X is independently selected form the group consisting of S, O and N, and each $R^{14}$ and $R^{15}$ is independently selected from the group consisting of alkyl, aryl, phenyl, alkylaryl, and arylalkyl.

The invention also relates to a method for preparing enantioselectively an enantiomeric equol or (compound (VI)):

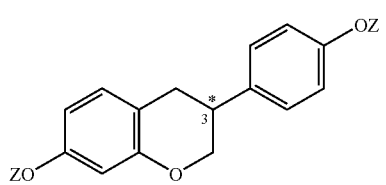

(VI)

wherein Z is H or PG, wherein PG is a hydroxyl protective group; comprising the steps of:
1) providing a 3-phenylchromene compound selected from:

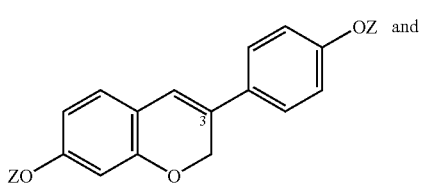

(VII)

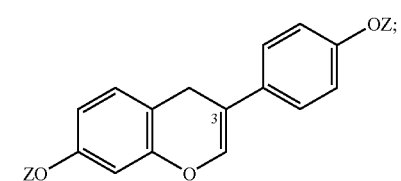

(VIII)

and
2) hydrogenating the 3-phenylchromene in the presence of an Ir catalyst having a chiral ligand shown as compound (V):

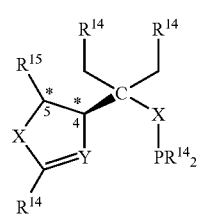

(V)

to form an enantiomeric equol, wherein each of Y and X is independently selected from the group consisting of S, O and N, and each $R^{14}$ and $R^{15}$ is independently selected from the group consisting of alkyl, aryl, phenyl, alkylaryl, and arylalkyl. When 3-phenylchromene compound is protected (X is PG), the protected enantiomeric equol compound (VI) can optionally be converted (for example: by acidification) to the enantiomeric equol, and analogs thereof.

The invention further relates to a method of preparing enantioselectively an enantiomeric equol, and analogs thereof, comprising the steps of: 1) reducing a 3-phenyl chromen-4-one to its corresponding chroman-4-one; 2) reducing the chroman-4-one to a corresponding chroman-4-ol; 3) dehydrating the chroman-4-ol to a corresponding chromene selected from 3-phenyl-3,4 chromene and 3-phenyl-2,3 chromene; and 4) hydrogenating the chromene in the presence of an Ir catalyst of compound (V) having a chiral ligand, to form the enantiomeric equol, and analogs thereof.

The invention further relates to the synthesis of enantioselective chromans, including enantiomeric equol, containing stable-isotopic atoms of $^{13}C$, $^{18}O$, or $^{2}H$, where such atoms are introduced in one of the intermediate steps in the preparation of the intermediate chromene or enantioselective chromane.

BRIEF DESCRIPTION OF THE DRAWINGS

FIGS. 1A, 1B, 1C and 1D show the Gas Chromatography Mass Spectrometry (GC-MS) trace and spectra, and the Liquid Chromatography Mass Spectrometry (LC-MS) trace and spectra, respectively, on a bis-MOM daidzein intermediate product in accordance with the present invention.

FIGS. 2A, 2B, 2C and 2D show the GC-MS trace and spectra, and the LC-MS trace and spectra, respectively, on a chroman-4-one intermediate product in accordance with the present invention.

FIGS. 3A, 3B, 3C and 3D show the GC-MS trace and spectra, and the LC-MS trace and spectra, respectively, on a chroman-ol product intermediate product (dehydrated) in accordance with the present invention.

FIGS. 4A, 4B, 4C and 4D show the GC-MS trace and spectra, and the LC-MS trace and spectra, respectively, on a bis-MOM-dehydroequol intermediate/product in accordance with the present invention.

FIGS. 5A, 5B, 5C and 5D show the GC-MS trace and spectra, and the LC-MS trace and spectra, respectively, on a MOM-protected S-equol product in accordance with the present invention.

FIGS. 6A and 6B show the LC-MS trace and spectra, respectively, on a S-equol product in accordance with the present invention.

FIGS. 7A, 7B, 7C and 7D show the GC-MS trace and spectra, and the LC-MS trace and spectra, respectively, on a MOM-protected R-equol product in accordance with the present invention.

FIGS. 9A and 9B show the GC-MS trace and spectra, respectively, on a TMS-derivatized S-equol products in accordance with the present invention.

FIGS. 9C and 9D show the GC-MS trace and spectra, respectively, on a TBDMS-derivatized S-equol products in accordance with the present invention.

FIGS. 10A and 10B show the GC-MS trace and spectra, respectively, on a TMS-derivatized R-equol products in accordance with the present invention.

FIGS. 10C and 10D show the GC-MS trace and spectra, respectively, on a TBDMS-derivatized R-equol products in accordance with the present invention.

DETAILED DESCRIPTION OF THE INVENTION

Definitions

Figure 1A:
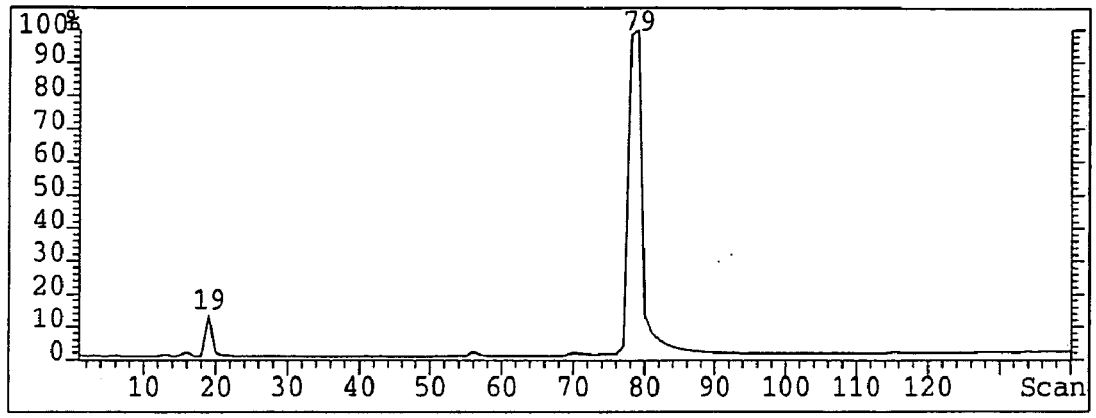

The term "enantioselective" refers to a chemical reaction that preferentially results in one enantiomer relative to a second enantiomer, i.e., gives rise to a reaction product of which one enantiomer, usually the desired enantiomer, has at least 10% of an enantiomeric excess (ee) in the reaction product.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

Enantioselective Hydrogenation of Chromene

An embodiment of the invention provides a method for preparing a chromane or substituted chromane having a chiral carbon contained within the heterocyclic ring and having a stereospecific configuration. A general structure of the resulting chromane compound is represented by compound (I), described herein before.

The chromane compound (I) illustrates substitution of the chromane with $R^2$ at the C-3 carbon position in the ring, such that only the C-3 carbon has chirality. In this case, when $R^2$ is a non-hydrogen substituent and only the C-3 carbon has chirality, then $R^1$ and R3 are H. The stereospecific configuration of the synthesized compound (I) at its chiral center (the C-3 carbon position) can be dictated by the stereospecific configuration of the chiral ligand of the iridium catalyst, which typically has at least one, and more typically two, or more, chiral carbon centers in the catalyst ligand, and by the type and molecular weight of any non-hydrogen substituents $R^1$, $R^2$ and $R^3$.

The starting compound for the chiral-selective hydrogenation is a corresponding chromene selected from compound (III) and (IV), described herein above.

Alternatively, the chromene compounds (III) or (IV) can be substituted with a non-hydrogen substituent at either the C-4 position ($R^3$) or at the C-2 position ($R^1$), providing alternatively chirality at the C-4 position or the C-2 position, respectively. When $R^1$ is a non-hydrogen substituent and only the C-2 carbon has chirality, then $R^2$ and $R^3$ are H; and when $R^3$ is a non-hydrogen substituent and only the C-4 carbon has chirality, then $R^1$ and $R^2$ are H.

The selected chiral catalyst system comprises an enantioselective iridium catalyst comprising a chiral ligand shown herein before as compound (V).

A more typical iridium-based catalyst comprises a chiral phosphine-oxazoline ligand of compound (IX), where $R^{14}$ and $R^{15}$ are earlier defined:

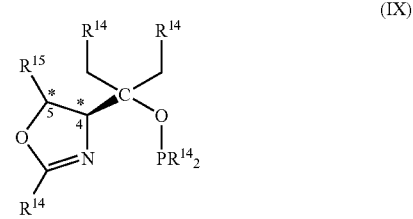

A preferred ligand compound is used wherein $R^{14}$ is phenyl and $R^{15}$ is methyl.

The phosphine-oxazoline ligand having a (4S,5S) configuration in the oxazoline ring can be synthesized from the starting material L-threonine (2S,3R) by the method described by in Theonine-Derived Phosphinite-Oxazoline Ligands for the Ir-Catalyzed Enantioselective Hydrogenation, *Adv. Synth. Catal.*, 2002, 344, pg. 40-44 (Menges and Pfaltz), incorporated herein by reference, and is available from Strem Chemical, Newburyport, Mass. The phosphine-oxazoline ligand having a (4R,5R) configuration in the oxazoline ring can be synthesized by the Menges and Pfaltz method where the starting material L-threonine is replaced with D-threonine (2R,3S).

The method has been shown to be highly stereospecific, typically forming enantiomeric chromanes having an enantiomeric excess (ee) of at least 10%, more typically at least 50%, more typically at least 90%, and even more typically at least 95%, and up to 100%, more typically up to 99.5%, and more typically up to 99%.

Prior to hydrogenation of the chromene compound (III) or (IV), any of $R^1$, $R^2$, $R^3$, $R^4$, $R^5$, $R^6$, or $R^7$, which are hydroxyl, can be protected with a hydroxyl protecting group PG. A typical protective group, methoxymethyl (-MOM) is employed by refluxing the early stage chromene precursors such as daidzein with methoxy methylchloride in the presence of diisopropyl ethyl amine. In other embodiments of the present invention, the chromene having unprotected hydroxyl substituents can be asymmetrically hydrogenated, typically in a polar solvent that improves the solubility of the unprotected chromene, such as, by example and without limitation, ethyl acetate, methanol, THF, N-methylpyrrolidone (NMP), dimethylformamide (DMF) and acetic acid.

Following hydrogenation, the protective group can be removed by acidification (for example, by excess HCl in methanol at between 0° C.-room temperature for 2 hours). Other acidic hydrolytic reagents (e.g acetic acid TFA as examples) can be used with differing rates of release of the protecting group. This step is also referred to as deprotecting of the compound.

The hydrogenation of the chromene is conducted in a polar solvent (typically dichloromethane) in hydrogen at pressures typically up to 200 psig, and at ambient temperature or higher. The reaction proceeds rapidly (within minutes) at catalyst concentrations of at least about 0.1 mol %, more typically at least about 0.5-2 mol %, and typically up to about 5 mol %, relative to the chromene.

Following enantioselective hydrogenation, the resulting enantiomeric chromane can be isolated from solvent, reactants and catalyst, and purified by chromatography on a silica gel plug filter, by procedures well known to those skilled in the art. The structure of the product can be confirmed by $^1$H and $^{13}C$ NMR analysis and by mass spectrometry with allied chromatography. The stereospecificity of the product can be confirmed by optical dichroism.

Enantiospecific Hydrogenation of 3-Phenylchromene to Prepare Enantiomeric Equol

In yet another embodiment of the invention, the method provides for preparation of an enantiomeric equol (7-hydroxy-3-(4'-hydroxyphenyl)-chroman).

The starting compound for the chiral-selective hydrogenation is a corresponding protected or unprotected 3-phenyl chromene selected from:

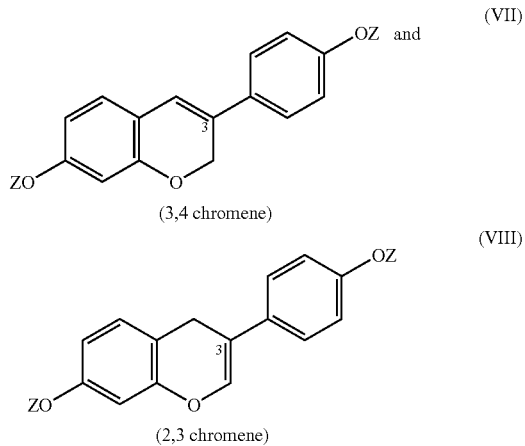

wherein Z is H or PG, wherein PG is a hydroxyl protective group, and wherein the hydroxyl groups at the C-7 position on the chromene and at the C-4 position of the 3-phenyl substituent have been protected, wherein PG is a hydroxyl protective group.

The selected chiral catalyst system comprises an iridium-based catalyst having a ligand shown as compound (III), described above. A more typical iridium-based catalyst comprises a phosphine-oxazoline ligand shown herein before as compound (IX). The preferred ligand is the compound shown herein before as compound (X).

Typical solvents that can be used in the synthesis include a lower alkyl dihalide such as dichloromethane, THF, and ethyl acetate. Other optional solvents, alone or in combination, include dimethylformamide (DMF), acetic acid, N-methylpyrrolidone (NMP), and methanol. Typically the reaction proceeds to completeness in dichloromethane at temperatures in the range of 0 to room temperature (rt), within a time period of 1 min to 3 hours and the hydrogen pressure from 0 psig (bubbling hydrogen through the mixture) up to 150 psig.

The literature discloses that the use of the (4S,5S)-phosphine-oxazoline ligand in the synthesis using functionalized linear alkenes resulted exclusively in R-configured alkanes and S-configuration for carbocyclic alkenes (A. Pfaltz, F. Menges. Adv. Synth. Catal. 2002, 344/1, pp 40-44, A. Pfaltz at al. Adv. Synth. Catal. 2003, 345/1-2, pp 33-43). No literature data were found for successful enantioselective hydrogenation of heterocyclic alkenes. In the synthesis using heterocyclic alkenes, the stereospecificity (as either S configuration or R configuration) of the substituted carbon of the synthesized heterocyclic alkane compound can either conform with, or oppose, the stereospecificity of the catalyst ligand. In one embodiment of the present invention, the use of the (4S,5S)-phosphine-oxazoline ligand in the synthesis using a functionalized heterocyclic alkene (the dehydroequol compound (VII)) resulted exclusively in the R-configured chromane (R-equol), while the use of the (4R,5R)-phosphine-oxazoline ligand resulted exclusively in an S-configured chromane (S-equol).

There is some indication, referred to in Example 9, that the hydrogenation of the 3-phenyl-3,4-chromene forms a corresponding 2,3-chromene intermediate, which then is hydrogenated to the chromane. In such case, the 3-phenyl-2,3-chromene may be a novel, isolated compound, and can be an alternative starting chromene for the enantioselective hydrogenation method of the present invention.

The synthesized enantiomer of equol can be converted into an equol analog or conjugate at the C-4' or the C-7 position with a conjugate selected from the group consisting of glucuronide, sulfate, acetate, propionate, glucoside, acetyl-glucoside, malonyl-glucoside, and mixtures thereof.

The resulting enantiomeric equol material typically has an enantiomeric excess (ee) of at least 10%, more typically at least 50%, more typically at least 90%, and even more typically of at least 95%, and typically up to 100%, more typically up to 99.5%, and more typically up to 99%.

An alternative starting material for the synthesis of equol is a chromen-4-one, such as a 3-phenyl-chromen-4-one, which is available naturally and commercially as daidzein or its methoxy analog, formononetin. Daidzein can be synthesized by known methods, such as that described in *J. Chem. Soc. Perkin Trans.*, 1991, pages 3005-3008, incorporated herein by reference. The starting daidzein can be protected (for example, with a protecting group PG, such as MOM). In a preferred synthesis route, purified bis-MOM daidzein, shown below as compound (XI), is hydrogenated to obtain a cis- and trans-mixture (1:1) of the corresponding 3-phenyl-chroman-4-one, shown as compound (XII):

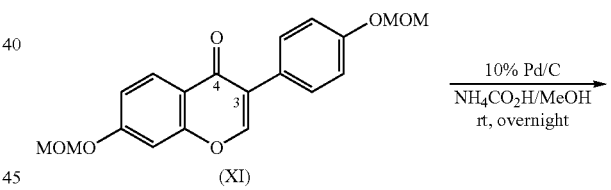

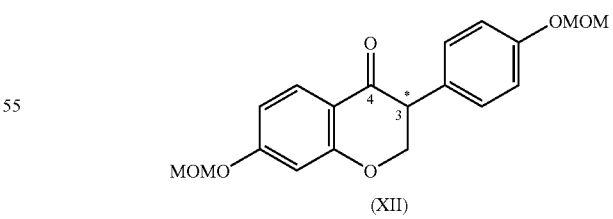

A 10% Pd/C catalyst and $NH_4CO_2H$ in methanol solvent was found suitable to convert the daidzein to the racemic chroman-4-one overnight at room temperature. The isolated 3-phenyl-chroman-4-one product is then reduced to a corresponding cis- and trans-mixture (about 3.4:1) of bis-MOM daidzein-ol (compound (XIII)) according to the reaction:

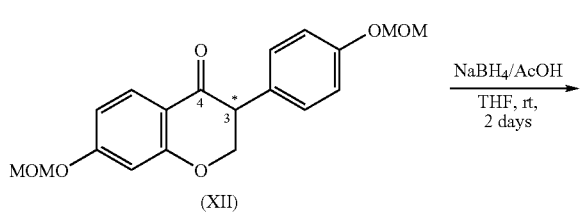

(XII)

NaBH₄/AcOH
THF, rt,
2 days

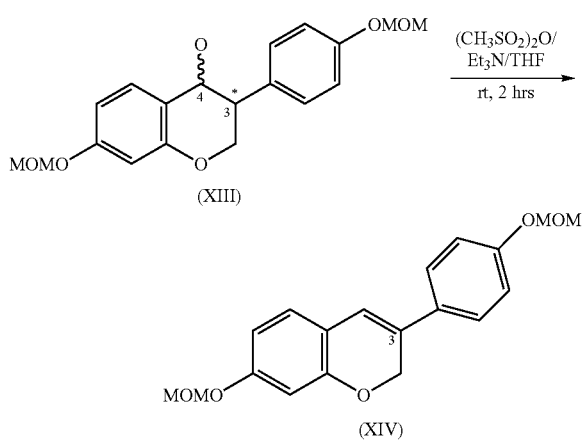

(XIII)

The bis-MOM daidzein-ol (a chromen-ol) is then dehydrated to introduce the double bond within the heterocylic ring, between the ring carbons in the 3 and 4 positions, resulting in formation of the 3,4-dehydroequol (compound (XIV)), according to the reaction:

(XIII)

(CH₃SO₂)₂O/
Et₃N/THF
rt, 2 hrs (XIV)

The 3,4-dehydroequol can be purified by crystallization to form a white solid (powder), which can be stabilized by storage in solid form in a freezer. The presence of air, moisture and storage in solvent for an extended time may cause decomposition of the dehydroequol.

A preferred Ir catalyst system comprises an IR-ligand complex (complex (XV)), comprised of the ligand shown as compound (V), with Ir and ((COD)Cl)2.

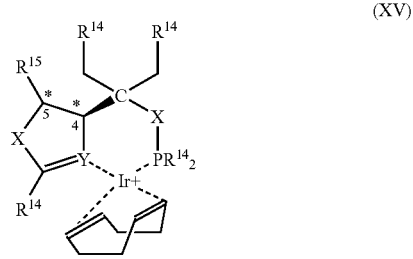

(XV)

An Ir-ligand complex can be obtained by refluxing the phosphine-oxazoline ligand with [Ir(COD)Cl]₂ in dichloromethane under standard conditions for about 1 hour. The Ir-ligand complex is then reacted with a counterion in aqueous dichloromethane to form the chiral Ir catalyst system as described by A. Pfaltz in Adv. Synth. Catal. 2002, 344/1, pp 40-44. A preferred iridium catalyst ligand comprises the phosphine-oxazoline ligand compound (IX) shown herein before. A preferred counterion is NaB(Ar$_f$)$_4$, shown as compound (XVI):

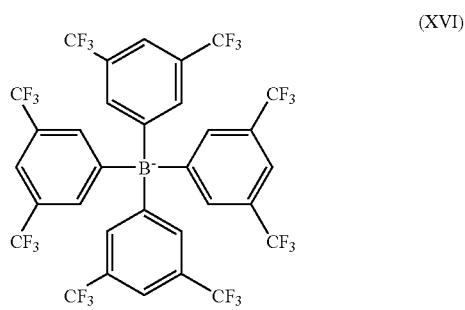

(XVI)

A functional group or substituent, such as a hydroxyl, sulfhydryl, or amino group, is termed "protected" when the substituent is modified to preclude undesired side reactions at the protected site. Suitable protecting groups for the compounds of the present invention will be recognized from the present application taking into account the level of skill in the art, and with reference to standard textbooks, such as Greene et al., *Protective Groups in Organic Synthesis* (New York: Wiley, 1991).

Non-limiting examples of hydroxyl-protecting groups useful in this embodiment include, without limitation: alkyl, typically methyl, ethyl, tert-butyl and benzyl; alkoxy alkyl, typically methoxy methyl ("MOM"), benzyloxy methyl, p-methoxy benzyl, and dimethoxy benzyl; silyl moieties, including trialkylsilyl such as triisopropylsilyl ("TIPS") and trimethylsilyl ("TMS") moieties; acyl moieties, such as acetyl and benzoyl; tetrahydropyranyl and related moieties; methylthiomethyl; and sulfonyl moieties, such as methane sulfonyl and benzene sulfonyl.

The protecting groups may be removed using conventional reagents and methods to give the unprotected chromane or chromene.

Use of Enantiomeric Equol

The synthesized stereoselective, enantiomeric equol compounds, S-equol and R-equol, can be used as the isolated enantiomer, or in a racemic (1:1) or non-racemic mixture, to make commercial and institutional products. The enantiomeric equol, or a composition or product made therefrom, can be consumed orally or applied topically, intradermally, subcutaneously, or inhaled in carrier, and can comprise a marketed or institutional food product, a pharmaceutical, an OTC medicament, an ointment, liquid, cream or other material suitable for topical application. A typical food composition can comprise at least 1 mg, and up to 200 mg, of the enantiomer of equol per serving. An orally-administered medicament can comprise at least 1 mg, and up to 200 mg, of the enantiomer of equol per dose. A product for topical application can comprise at least 0.1%, and up to 10%, by weight of the enantiomer of equol.

Enantiomeric equol, or a composition or preparation made therefrom, can be administered to subjects for the treatment and/or prevention of, or for reducing the predisposition to, diseases and conditions related thereto. Compositions or products can also include one or more pharmaceutically acceptable adjuvants, carriers and/or excipients. Other compositions and products that can be made from enantiomeric equol, and their uses in the treatment or prevention of diseases and conditions, are disclosed in PCT Publication WO 2004/23056, published Jan. 29, 2004, and in PCT Publication WO 2004/039327, published May 13, 2004, incorporated herein by reference.

Methods

A. Method for synthesizing (4R,5R)-phosphine-oxazoline ligand

The (4R,5R)-phosphine-oxazoline ligand, shown herein before as compound (X), was synthesized substantially in accordance with Examples A12 and B12 of U.S. Pat. No. 6,632,954, issued to Pfaltz et al, and incorporated herein by reference. Whereas Pfaltz started out with L-threonine and produced the (4S,5S)-phosphine-oxazoline, this method starts out with D-threonine.

a) Preparation of D-Threonine methyl ester

A solution of gaseous HCl in methyl alcohol (210 mL of 2N, or 0.46 mol) was placed in a 0.5 L 3 neck round bottom flask equipped with a magnetic stirrer, thermocouple, nitrogen line, condenser and heating mantle. A total of 25.1 g (0.21 mol) of D-threonine (98%, Aldrich) was added to the HCl/MeOH solution at room temperature and resulted mixture was refluxed overnight. The reaction was monitored by TLC using EtOAc/MeOH/AcOH=7:2.5:0.5 mixture as a mobile phase. The reaction was stopped when all D-threonine was essentially consumed ($R_f$=0.39 for D-threonine methyl ester, gives a "carrot"—hued spot with ninhydrin, and $R_f$=0.19 for D-threonine—a red spot with ninhydrin). A solvent was removed on rotavap to yield 39.49 g (110% yield) of a glass-looking material, which was used in the next step without purification.

b) Preparation of N-benzoyl-D-threonine methyl ester

A crude D-threonine methyl ester (39.49 g) was dissolved in 300 mL of methanol and than transferred to the 1 L 3-neck round bottom flask equipped with a thermocouple, magnetic stirrer and cooling ice bath. A solution was chilled to 12° C., and a total of 64.1 g (0.63 mol, 3 eq.) was added to the flask and then cooled to −10° C. A total of 30.9 g (0.21 mol) of benzoyl chloride was added to the solution and resulting mixture stirred at 0° C. for 1 hour. After this period of time the solvent was removed on rotavap to yield a viscous semi-solid. A total of 300 mL of cold water was added to the residue and organic material was extracted with ethyl acetate (2×300 mL). The organic phase was separated, washed with brine (200 mL) and dried over sodium sulfate. The solvent was removed on rotavap to yield 52.02 g (104%) of a clear yellow oil with Rf=0.39 in EtOAc/hexane=6:4). Obtained oil was crystallized from 200 mL of ether to give a white solid, which was filtered off, washed with hexane (2×100 mL) and dried under suction. An additional drying in a vacuum desiccator yielded 42.35 g (84.7% yield in 2 steps).

$^1$H-NMR (300 MHz, CDCl$_3$, δ): 1.25 (d, J=6.3 Hz, 3H, CH$_3$), 3.42 (d, 1H, OH), 3.78 (s, 3H, OCH$_3$), 4.42 (dq, J=2.6 Hz, J=6.3 Hz, 1H, CH—O), 4.78 (dd, J=2.4 Hz, J=8.7 Hz, 1H, CH—N), 7.2 (bd, J=9.0 Hz, 1H, NH), 7.40 (t, J=7.3 Hz, 2H, Ph), 7.43 (t, J=7.3 Hz, 1H, Ph), 7.82 (d, J=7.3 Hz, 2H, Ph).

$^{13}$C APT NMR (75 MHz, CDCl$_3$, δ): 19.94, 52.47, 57.79, 67.97, 127.14, 128.48, 131.80, 133.56, 168.07, 171.49.

c) Preparation of (4R,5R,)-5-methyl-2-phenyl-4,5-dihydrooxazole-4-carboxylic acid methyl ester An excess of thionyl chloride (75 mL) was placed in a 250 mL round bottom flask equipped with a thermocouple, magnetic stirrer, caustic scrubber and cooling dry ice/acetone bath and was cooled to −35° C. A solid N-benzoyl-D-threonine methyl ester (25.75 g, 0.108 mol) was added portion-wise to the flask while maintaining reaction temperature at −20° C. After completed addition, the resulting mixture was slowly warm up to room temperature and stirred for additional 1 hour. The reaction was kept overnight at ~5° C. after that an excess of thionyl chloride was removed under vacuum at ~30° C. Obtained oil was washed with saturated cold sodium bicarbonate (1.5 L), extracted with dichloromethane (3×200 mL) and the organic phase was dried over sodium sulfate. The solvent was removed on rotavap to yield 22.93 g of clear oil. This oil was purify on 13×9 cm silica gel plug using CH$_2$Cl$_2$/hexane=1:1 as eluent to give 19.88 g (83.6% yield) of clear oil which slowly crystallized to white solid ($R_f$=0.17 in CH$_2$Cl$_2$/hexane=1:1).

$^1$H-NMR (300 MHz, CDCl$_3$, δ): 1.40 (d, J=6.3 Hz, 3H, CH$_3$), 3.80 (s, 3H, OCH$_3$), 4.97 (d, J=10.2 Hz, 1H, CH—N=C), 5.05 (J=6.0 Hz, J=10.2 Hz, 1H, CH—O), 7.41 (t, J=7.5 Hz, 2H, Ph), 7.50 (t, J=7.3 Hz, 1H, Ph), 7.43 (t, J=7.3 Hz, 1H, Ph), 8.00 (d, J=7.3 Hz, 2H, Ph).

$^{13}$C NMR (75 MHz, CDCl3, δ): 16.13, 51.96, 71.67, 77.55, 127.17, 128.21, 128.44, 131.69, 166.06, 170.31.

d) Preparation of (4R,5R)-2-(5-Methyl-2-phenyl-4,5-dihydrooxazol-4-yl)-1,3-diohenyl-propan-2-ol A solution of 8.61 g (39.27 mmol) of (4R,5R,)-5-methyl-2-phenyl-4,5-dihydrooxazole-4-carboxylic acid methyl ester in 200 mL of anhydrous diethyl ether was placed in a 200 mL three neck round bottom flask equipped with a thermocouple, nitrogen line, magnetic stirrer and cooling dry ice/acetone bath. A total of 120 mL (120 mmol, 3 eq.) of 1M solution of benzylmagnesium chloride in diethyl ether was added to the reaction at −78° C. via syringe. The cooling bath was removed, and the reaction mixture was allowed to warm up to room temperature whiting 2 hours and stirred for one hour at this temperature. Resulted milky solution was poured on cold aqueous solution of ammonium chloride (1.2 L) and extracted with ethyl acetate (2×200 mL). The organic layer was washed with water (200 mL) and brine (100 mL). After drying over sodium sulfate the solvent was evaporated under reduced pressure to afford 16.95 g of clear oil. The crude product was purified on silica gel column using hexane/ethyl acetate=25/1 mixture as eluent to yield 13.75 g (86% yield) of pure material as a white foam/powder with $R_f$=0.49 in EtOAc/hexane=1:9.

$^1$H-NMR (300 MHz, CDCl$_3$, δ): 1.70 (d, J=6.6 Hz, 3H, CH$_3$), 2.10 (s, 1H, OH), 2.67 (d, J=13.8 Hz, 1H, CH$_2$), 2.92 (J=13.8 Hz, 1H, CH$_2$), 3.11 (d, J=14.1 Hz, 1H, CH$_2$ 3.17 (d, J=13.8 Hz, 1H, CH$_2$), 4.10 (d, J=9.3 Hz, 1H, CH—N=C), 4.81 (dq, J=6.9 Hz, J=9.3 Hz, 1H, CH—O), 7.20-7.30 (m, 13H, Ph), 8.05 (d, J=7.3 Hz, 2H, Ph).

$^{13}$C NMR (75 MHz, CDCl$_3$, δ): 16.70, 42.22, 42.75, 71.81, 76.13, 79.34, 126.42, 128.08, 128.10, 128.23, 130.95, 131.31, 137.11, 137.22, 164.06.

e) Preparation of (4R,5R)-O-[1-Benzyl-1-(5-methyl-2-phenyl-4,5-dihydrooxazol-4-yl)-2-phenylethyl]-diphenyl-phosphinite A solution of 6.64 g (16.44 mmol) of (4R,5R)-2-(5-Methyl-2-phenyl-4,5-dihydrooxazol-4-yl)-1,3-diphenyl-propan-2-ol in 200 mL of anhydrous pentane was placed in a 500 mL three neck round bottom flask equipped with thermocouple, nitrogen line, magnetic stirrer and cooling dry ice/acetone bath.

A total of 13 mL (20.8 mmol, 1.26 eq.) of 1.6M solution of n-butyl lithium in hexane was added to flask at −78° C. followed by addition of 4.32 g (37.17 mmol, 2.26 eq.) N,N,N′,N′-tetramethylethylenediamine. The cooling bath was removed and the mixture was warmed up to 0° C. whiting 1 hour and stirred an additional 1.5 hour. After this period of time, a total of 4.10 g (18.58 mmol) of diphenylchlorophosphine was added to the reaction, and resulting mixture was allowed to warm up to room temperature. After stirring at this temperature for 3 hours, the solvent was removed on rotovap and off-white semisolid was obtained. The crude product was dissolved in minimal amount of dichloromethane and than purified via silica gel plug using EtOAc/hexane=1:20 as an eluent to yield 8.78 g (96% yield) of white foam with Rf=0.56 in EtOAc/hexane=1:9. The isolated foam was purified one more time using silica gel column and EtOAc/hexane=1:50 to give 5.56 g (61% yield) of pure product as a bulky white powder.

f) Preparation of Sodium tetrakis [3,5-bis-(trifluoromethyl)-phenyl]-borate (as described by D. L. Reger, T. D. Wright, C. A. Little, J. J. S. Lamba, M.D. Smith in *Inorg. Chem.*, 2001, 40, 3810-3814)

Step f-1: A total of 3.49 g (31.7 mmol, 1 eq.) of sodium tetrafluoroborate, 4.98 g (205 mmol, 6.45 eq.) and 600 mL of anhydrous ether were charged in a 2 L 4 neck round bottom flask, equipped with overhead stirrer, addition funnel, thermocouple, condenser, nitrogen line and heating mantle. Dibromoethane (~1 mL) was added, and the flask was gently heated to initiate the reaction. The heat was removed, and a solution of 50.94 g (174 mmol, 5.47 eq.) of 3,5-bis-(trifluoromethyl)-bromobenzene in 100 mL of ether was added dropwise within 30 min, which caused the solution to gently reflux. Once all bromide was added, the reaction was heated with a heating mantle to continue the reflux for an additional 1 hour. The heat than was removed, and the resulted mixture stirred overnight at room temperature. After this period of time, the reaction mixture was poured on a cold solution of sodium carbonate (77 g of $Na_2CO_3$ in 950 mL of water) and stirred for 30 min. The top brown organic layer was separated, and the bottom milky aqueous layer was extracted with ether (2×300 mL). Combined organic phases were dried over sodium sulfate and stirred with 17 g of charcoal for 2 hours at room temperature. The mixture was filtered through the Celite pad, and the ether was removed on a rotovap to yield 32.4 g of brown semisolid. The obtained crude product was dissolved in 800 mL of benzene and water was removed with a Dean-Stark trap by azeotropic distillation for 3 hours. The solvent volume was reduced to about 200 mL and the residue was cooled on an ice bath to form a mixture of a solid and heavy brown oil. The heterogeneous mixture was filtered off, washed with benzene (3×50 mL) followed by hexane wash (1×100 mL). The isolated solid was dried under suction and nitrogen flow to yield 13.28 g (47% yield) of white solid with $R_f$=0.15 in EtOAc.

Step f-2: Chiral (4R,5R)-Iridium Complex: (by analogy with the synthesis of 4S,5S-iridium complex described by A. Pfaltz in Adv. Synth. Catal. 2002, 344/1, pp 40-44). A solution of 5.49 g (9.88 mmol, 1.82 eq.) of (4R,5R)-O-[1-Benzyl-1-(5-methyl-2-phenyl-4,5-dihydrooxazol-4-yl)-2-phenyl-ethyl]-diphenyl-phosphinite in 150 mL dichloromethane was placed in a 500 mL three neck round bottom flask equipped with a thermocouple, magnetic stirrer, condenser, nitrogen line and a heating mantle. A total of 3.65 g (5.43 mmol, 1 eq.) of the iridium complex $[Ir(COD)Cl]_2$ was added portion-wise to the flask and formed red solution was refluxed for 2 hours. The heating mantle was removed, and 10.25 g (11.56 mmol, 1.17 eq.) of solid sodium tetrakis[3,5-bis-(trifluoromethyl)-phenyl]-borate was added to the reaction mixture. The resulted mixture vigorously stirred for 5 min and after that was diluted with 130 mL of water. The heterogeneous mixture stirred for an additional 15 min and the layers were separated. The aqueous phase extracted with dichloromethane (2×100 mL) and combined organic layers dried over sodium sulfate. The solvent was evaporated under reduced pressure to afford 19.05 g of orange foam. The obtained crude material was purified via silica gel plug (366 g of $SiO_2$) using $CH_2Cl_2$/hexane=1:1 as an eluent. The solvent was removed on rotovap to give 14.81 g (79% yield) of the catalyst as a bright orange powder with $R_f$=0.28 in $CH_2Cl_2$/hexane=6:4.

B. Method for TMS and TBDMS Derivitization a. TMS: 20 µg of R-Equol and S-Equol were placed into separate derivitization vials and dried down under nitrogen. Six drops of Tri-Sil Reagent were added to each vial using a glass pipet, and the contents heated for 30 minutes at 65° C. The treated sample was dried under nitrogen and reconstituted in 50 µL of hexane. The sample was then run via GC/MS.

b. TBDMS: 20 µg of R-Equol and S-Equol were placed into separate derivitization vials and dried down under nitrogen. An amount of 100 µL of Acetonitrile and 100 µL of MTB-STFA+1% t-BDMCS were added to each vial, and the contents heated for 1 hour at 100° C. The treated sample was dried under nitrogen and reconstituted in 50 µL of hexane. The sample was then run via GC/MS.

C. GC/MS and LC/MS Analysis

GCMS: Products and intermediate products were analyzed using a VG Autospec magnetic sector mass spectrometer equipped with an HP Gas Chromatograph 5890 series II. A solid glass needle injector was used to inject samples onto a J&W Scientific DB1 column, 0.25 mm I.D., 0.25 µm film using helium as the carrier gas. A temperature gradient starting at 225° C. for 1.0 min, then ramped to 310° C., and held for 10 min was used before making the next injection. The EI+ magnetic scan experiment was used to acquire fullscan traces and spectrum of all products with a mass range of 100-900.

LCMS: Products and intermediate products were analyzed using a Water Quattro Micro API tandem mass spectrometer equipped with a Waters Acquity UPLC. The two mobile phase system using water, 2 mM ammonium acetate (mobile phase A) and methanol, 2 mM ammonium acetate (mobile phase B) with 0.1% formic acid was held isocratic at 50/50. A rheodyne injector was plumbed immediately before the probe, allowing for direct loop injections into the instrument. The MS experiment with capillary potential 3.5 kV, cone 18V, a collision gas of 18, mass range 100-500, under ESI+ was created to acquire the fullscan traces and spectrum of all products.

EXAMPLES

Example 1

Synthesis of the MOM-protected chromen-one (bis-MOM Daidzein, 7-methoxymethoxy-3-(4'-methoxymethoxy-phenyl)-2H-chromen-4-one)

A total of 329 g (1.29 mol) of 97% daidzein (from LLC Laboratories) was mixed with 4.5 L of dichloromethane in a 12 L 4-neck round bottom flask equipped with a thermocouple, overhead stirrer, heating mantle, addition funnel and nitrogen line. The resulted white suspension was chilled to 8° C., and a total of 655.8 g (5.07 mol, 3.9 eq.) of diisopropylethylamine (DIEA) was added to the pot. After 20 min a total of 373 g (4.63 mol, 3.59 eq.) of chloromethylmethyl ether (MOM-Cl) was added to the mixture via an addition funnel at 8° C. An ice bath was removed, replaced with a heating mantle and allowed to warm up to room temperature within 2 hours. The pot temperature was maintained at 40° C. and reaction was kept (usually overnight) at this temperature until daidzein and mono-MOM intermediate disappeared according to TLC ($R_f$=0.23 for daidzein, 0.38 for mono-MOM and 0.62 for bis-MOM-daidzein in EtOAc/hexane=1:1). The resulted clear brown solution was cooled to room temperature, and slowly poured under agitation on a cold mixture of 4 L of water, 1 kg of ice, 1 L of saturated sodium bicarbonate and 3 L of dichloromethane, which was prepared in a 20 L plastic bucket equipped with a powerful overhead stirrer and thermocouple. The pH of the resulted solution must stay basic during this work up to avoid degradation of the product. The organic phase was separated, and aqueous was back extracted with dichloromethane (2×1 L). The organic layers were combined, washed with water (2×3 L), sodium bicarbonate (3 L) and dried over sodium sulfate (500 g). The solvent was removed under reduced pressure to give 431 g (97% yield) of the product as a yellow solid. This material was purified by crystallization from 3.5 L of hot (56° C.) ethyl acetate followed by filtration and consequent washes with EtOAc/hexane=3:1 (2 L). Separated solid was dried overnight at 35° C. in a vacuum oven to yield 340.6 g (77% isolated yield) of bis-MOM-daidzein as a white solid. A second crop (a total of 66.31 g of the product) was isolated from a mother liquor to give a bis-MOM-daidzein in the 91.78% combined yield.

Figure 1B:
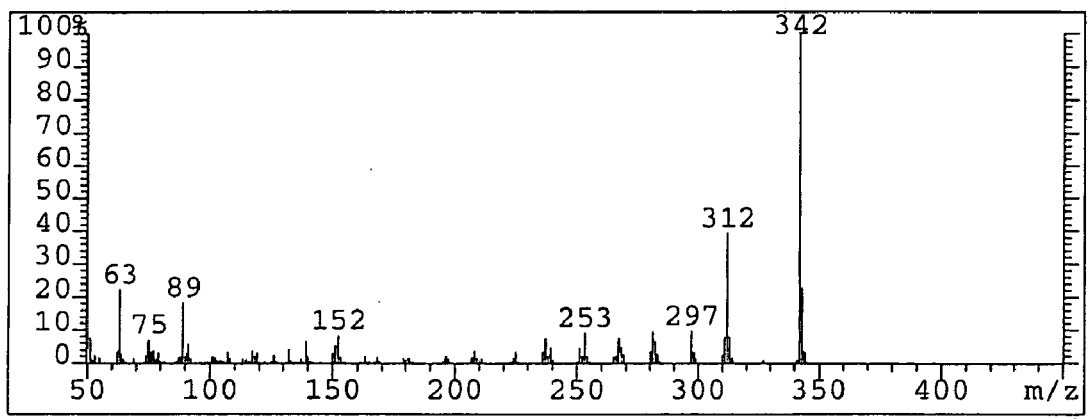

Gas Chromatography Mass Spectrometry (GC-MS) traces and spectra were obtained on the bis-MOM Daidzein product according to the GC-MS Method described in the Methods Section, and are shown in FIGS. 1A and 1B, respectively. Liquid Chromatography Mass Spectrometry (LC-MS) traces and spectra were obtained on the bis-MOM Daidzein product according to the LC-MS Method described in the Methods Section, and are shown in FIGS. 1C and 1D, respectively.

$^1$H NMR and $^{13}$C NMR data appear below.

$^1$H NMR (300 MHz, CDCl$_3$, δ): 8.21 (d, 1H, J=9.3 Hz), 7.92 (s, 1H), 7.48 (d, 2H, J=9.0 Hz), 7.07 (m, 4H), 5.26 (s, 2H, OCH$_2$O), 5.20 (s, 2H, CH$_2$O), 3.50 (s, 3H, CH$_3$O), 3.48 (s, 3H, CH$_3$O).

$^{13}$C NMR (75 MHz, CDCl$_3$, δ): 175.697, 161.337, 157.543, 152.228, 130.045, 127.716, 125.329, 124.690, 119.076, 116.147, 115.370, 102.969, 94.280, 56.290, 55.861.

Example 2

Hydrogenating the chromen-one to a chroman-one (7-methoxymethoxy-3-(4'-methoxymethoxy-phenyl)chroman-4-one)

A total of 336.5 g (0.983 mol) of bis-MOM-daidzein and 3.3 L of methanol were charged in a 12 L 4-neck round bottom flask equipped with a condenser, thermocouple, overhead stirrer, heating mantle and nitrogen line. A solid ammonium formate (309.4 g, 4.906 mol, 5 eq.) was added to the flask under agitation and a resulting slurry stirred for 20 min at room temperature. A total of 23.2 g (6.89 wt %) of dry 10% Pd/C was carefully transferred to the pot under nitrogen atmosphere and the reaction temperature was maintained at 45° C. The reaction was monitored by TLC ($R_f$=0.22 for bis-MOM-daidzein and 0.29 for the product in EtOAc/hexane=2:8) until all starting material disappeared (usually it requires 5 hours). Warm (~30° C.) reaction mixture was filtered through Celite (142 g) in order to remove the catalyst, and the filter was washed with 2 L of dichlorometane. Organic filtrates were combined, and the solvent was removed under reduced pressure to give a yellow solid, which was recrystallized from methanol-hexane to yield 241.2 g (71.3% yield) of the product as a white solid. An additional amount (36.94 g) was isolated from a mother liquor to give the product in 82.2% combined yield.

GC-MS traces and spectra of the chroman-4-one product are shown in FIGS. 2A and 2B, respectively. LC-MS traces and spectra of the chroman-4-one product are shown in FIGS. 2C and 2D, respectively.

$^1$H NMR and $^{13}$C NMR data appear below.

$^1$H NMR (300 MHz, CDCl$_3$, δ): 9.0 (d, 1H, J=9.0 Hz), 7.95 (dd, 2H, J=9.0 Hz, J=2.4 Hz), 7.00 (dd, 2H, J=9.0 Hz, J=2.4 Hz), 6.70 (dd, 1H, J=8.7 Hz, J=2.1 Hz), 6.62 (d, 1H, J=2.4 Hz), 5.20 (s, 2H, OCH$_2$O), 5.15 (s, 2H, OCH$_2$O), 4.62 (d, 1H, CH$_2$O, J=0.6 Hz), 4.60 (d, 1H, CH$_2$O, J=2.7 Hz), 3.87 (dd, 1H, CH, J=7.8 Hz, J=6.0 Hz), 3.47 (s, 3H, CH$_3$O), 3.45 (s, 3H, CH$_3$O).

$^{13}$C NMR (75 MHz, CDCl$_3$, δ): 190.98, 163.441, 163.174, 156.686, 129.560, 129.423, 128.516, 94.312, 94.029, 71.782, 56.290, 55.853, 51.145.

Example 3

Reducing the chroman-one to a chroman-ol (7-methoxymethoxy-3-(4'-methoxymethoxy-phenyl)chroman-4-ol) as a mixture of cis- and trans-isomers A total of 25.33 g (0.67 mol) of solid sodium borohydride was charged in a 12 L 4-neck round bottom flask equipped with a thermocouple, overhead stirrer, cooling ice/methanol bath, addition funnel and nitrogen line. A total of 3 L of dry THF was added to the flask and resultant suspension was cooled to 1.4° C. The glacial acetic acid (52.54 g, 0.875 mol) was slowly added to the flask as a solution in 200 mL of THF, and the mixture stirred at 10° C. for 20 min. The reaction was cooled to −4° C. and a solution of 230.1 g (0.668 mol) of bis-chroman-4-one in 1.3 L of THF was added to the flask. The reaction slowly agitated for three days at room temperature and monitored by TLC until all starting ketone disappeared. The reaction was quenched by addition to 12 L of cold saturated solution of ammonium chloride, organic layer was separated, and aqueous phase was extracted with dichloromethane (2×1 L). Combined organic phases washed with water (1×3 L) and dried over sodium sulfate. Solvent was removed under reduced pressure to yield 229.7 g (99.2% yield) of the product as a colorless viscous oil (as a mixture of cis-trans=3:1 isomers). This material was used in next step without any purification.

Figure 3C:
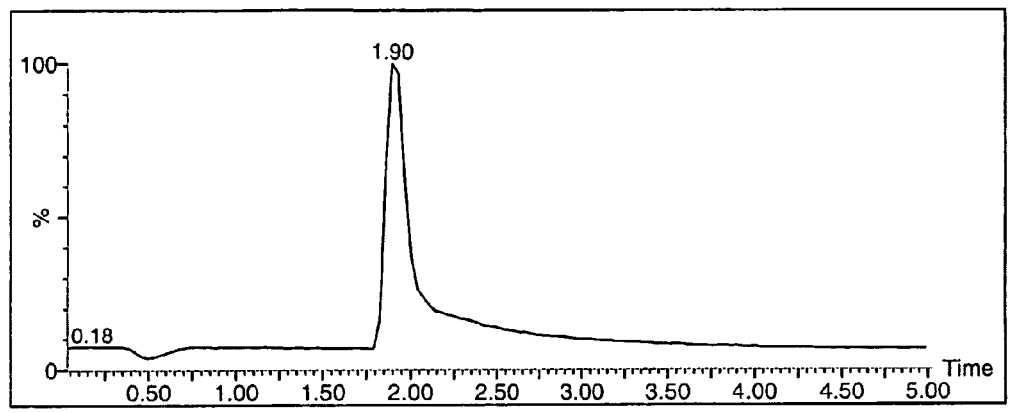
Figure 3D:
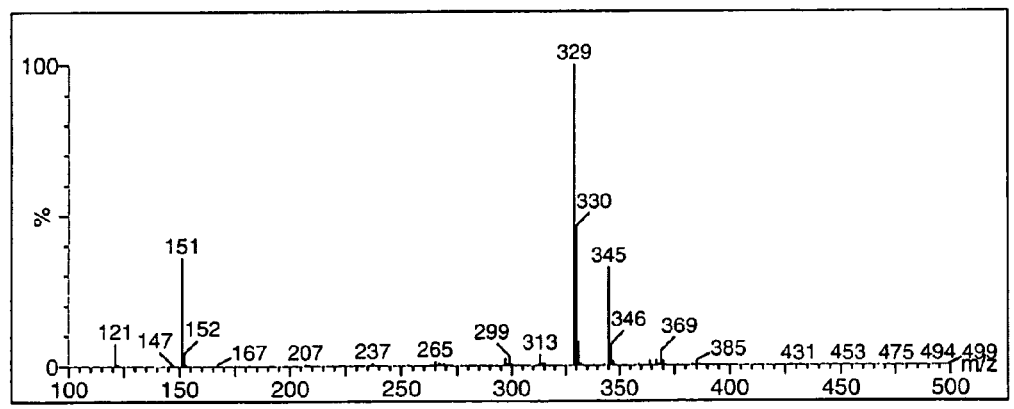

GC-MS traces and spectra of the chroman-ol product are shown in FIGS. 3A and 3B, respectively. LC-MS traces and spectra of the chroman-ol product are shown in FIGS. 3C and 3D, respectively. Each mass spec analysis provided a MW for the chroman-ol product as 328, whereas the actual MW of 346, a difference of 18. Since the NMR data confirm the structure of the product, it is believed that the chroman-ol product may have dehydrated during the ionization of the sample during the mass spec analyses, resulting in a loss of one water molecule, which caused the charged molecular ion in the mass spectrometric analysis to appear 18 a.m.u. lower in mass.

$^1$H NMR and $^{13}$C NMR data appear below.

$^1$H NMR (300 MHz, CDCl$_3$, δ, trans-isomer): 7.32 (d, 1H, J=8.7 Hz), 7.12 (dd, 2H, J=8.7 Hz, J=2.1 Hz), 6.98 (dd, 2H, J=8.4 Hz, J=1.8 Hz), 6.63 (dd, 1H, J=8.4 Hz, J=2.7 Hz), 6.54 (d, 1H, J=2.4 Hz), 5.12 (s, 4H, OCH$_2$O), 4.81 (dd, 1H, CHOH, J=7.5 Hz, J=5.1 Hz), 4.30 (dd, 1H, CH$_2$O, J=10.8 Hz, J=3.3 Hz), 4.18 (dd, 1H, CH$_2$O, J=11.4 Hz, J=8.4 Hz), 3.44 (s, 6H, CH$_3$O), 3.04 (ddd, 1H, CH, J=11.4 Hz, J=8.3 Hz, J=3.3 Hz), 2.27 (d, 1H, OH).

For cis-isomer: 7.20-7.10 (m, 3H), 7.05-6.95 (m, 2H), 6.68-6.52 (m, 2H), 5.14 (s, 2H, OCH2O), 5.13 (s, 2H, OCH$_2$O), 4.68 (br.s, 1H), 4.51 (dd, 1H, J=12.0 Hz, J=10.5 Hz), 4.3-4.1 (m, 1H), 3.45 (s, 6H, CH$_3$O), 3.23 (ddd, 1H, J=11.7 Hz, J=6.6 Hz, J=3.3 Hz).

$^{13}$C NMR (75 MHz, CDCl$_3$, δ trans-isomer): 157.964, 156.443, 131.971, 129.366, 129.204, 128.921, 118.331, 116.608, 109.489, 109.327, 103.810, 94.337, 94.304, 69.023, 68.069, 55.910, 55.877, 46.186.

Example 4

Dehydration of the chroman-ol to the chromene bis-MOM-dehydroequol (7-methoxymethoxy-3-(4'-methoxymethoxy-phenyl)-2H-chromen)

A solution of 227.7 g (0.658 mol) of the above alcohol (as a mixture of cis-trans isomers) was dissolved in 3.5 L of THF and transferred in a 12 L 4-neck round bottom flask equipped with a thermocouple, overhead stirrer, cooling ice/methanol bath, addition funnel and nitrogen line. A total of 667.3 g (6.58 mol) of Et$_3$N was added to the alcohol solution at −8° C. followed by addition of 222.7 g (1.28 mol) of methanesulfonic acid anhydride in 1.5 L of THF. The reaction was allowed to warm up to room temperature while monitoring by HPLC and stirred until all alcohol disappeared (about 2 hours). The reaction was quenched by addition to the 10 L of cold water. The organic layer was separated, and the aqueous phase extracted with dichloromethane (2×2 L). Combined organic layers were washed with water (2×3 L) and dried over sodium sulfate. Solvent was removed under reduced pressure to form a viscous semisolid material. The resulted mixture was diluted with hexane (1.5 L) and cooled on an ice. Precipitated solid was filtered off, washed with hexane (2×1 L) and dried under nitrogen to give 136 g (63% yield) of bis-MOM-dehydroequol as a white solid. Additional 10 g was isolated from mother liquor to give a total of 146 g of the product in 69% combined yield. Isolated alkene (131.6 g) was additionally purified on silica gel plug using dichloromethane as an eluent to yield 124.8 g (94.8% recovery) of bis-MOM-dehydroequol as a white solid. This material was used for asymmetric hydrogenation.

GC-MS traces and spectra of the bis-MOM-dehydroequol product are shown in FIGS. 4A and 4B, respectively. LC-MS traces and spectra of the bis-MOM-dehydroequol product are shown in FIGS. 4C and 4D, respectively.

$^1$H NMR and $^{13}$C NMR data appear below.

$^1$H NMR (300 MHz, CDCl$_3$, δ): 7.33 (dd, 2H, J=8.7 Hz, J=2.1 Hz), 7.03 (dd, 2H, J=8.7 Hz, J=1.8 Hz), 6.97 (d, 1H, J=9.0 Hz), 6.67 (s, 1H, HC=C), 6.59 (dd, 2H, J=7.2 Hz, J=2.4 Hz), 5.17 (s, 2H, OCH$_2$O), 5.14 (s, 2H, OCH$_2$O), 5.09 (d, 2H, OCH$_2$C=C, J=1.2 Hz), 3.46 (s, 6H, CH$_3$O).

$^{13}$C NMR (75 MHz, CDCl$_3$, δ): 157.883 (C7), 156.855 (C9), 154.153 (C4'), 130.596 (C10), 128.816 (C3), 127.360 (C8), 125.750 (C6), 118.323 (C4), 117.401 (C1'), 116.390 (C3'), 109.319 (C5), 103.842 (C2'), 94.377 (OCH$_2$O), 94.329 (OCH$_2$O), 67.171 (C2), 55.958 (CH$_3$O).

Example 5

Enantioselective hydrogenation of bis-MOM dehydro-equol to MOM-protected S-equol ((S)-7-(methoxymethoxy)-3-(4'-methoxymethoxy)-phenyl chroman)

A solution of 60.48 g (0.184 mol) of bis-MOM-dehydroequol and 3.10 g (0.0018 mol, 1 mol %) of ((4R,5R)-(−)-O-[1-Benzyl-1-(5-methyl-2-phenyl-4,5-dihydro-oxazol-4-yl)-2-phenylethyl]-diphenylphosphinite-(1,5-COD)-iridium(I) tetrakis-(3,5-bis-trifluoromethyl)-phenylborate in 1.3 L of dichloromethane was placed in a 2 L glass reactor equipped with a magnetic stirrer, thermocouple, gas inlet tube and a pressure relief valve. The air was replaced with nitrogen followed by hydrogen purge, and a 60 psig hydrogen pressure was maintained. The reaction mixture was monitored with TLC (R$_f$=0.26 for starting bis-MOM-dehydroequol, greenish spot with PMA on hot plate, and R$_f$=0.28 for bis-MOM-equol, a purple spot with PMA, in ethyl acetate/hexane=1:9). The reaction can be monitored by GC-MS (HP 5890 and MS 5972 were used, column DB-5 MS, 30 m length, 0.25 mm ID, 0.25 μm film, He carrier gas, flow rate 1.7 mL/min. Temp. program: 50° C. for 1 min, 20° C./min to 300° C., hold at 300° C. for 5 min, run time is 18.5 min. Retention time for the product is 15.77 min, and 16.41 min for the starting material).

The reaction was kept at 60 psig hydrogen pressure for 110 min until all starting material is consumed. Hydrogen was immediately replaced with nitrogen and clear red solution was quenched with a cold ammonium chloride solution (1 L of saturated ammonium chloride and 2 kg of ice). The organics were extracted with dichloromethane (2×1 L), combined organic phases were washed with 2 L of water and dried over sodium sulfate. Solvent was removed on rotavap and a red oil was purified on silica gel using ethyl acetate/hexane=2:8 mixture as an eluent to yield 42.8 g (70.3% yield) of bis-MOM-equol as a white solid with mp 37-38° C.

GC-MS traces and spectra of the MOM-protected S-equol product are shown in FIGS. 5A and 5B, respectively. LC-MS traces and spectra of the MOM-protected S-equol product are shown in FIGS. 5C and 5D, respectively.

$^1$H NMR and $^{13}$C NMR data appear below.

$^1$H NMR (300 MHz, CDCl$_3$, δ): 7.16 (d, 2H, J=8.7 Hz), 7.02 (d, 2H, J=8.7 Hz), 6.9 (s, 1H), 6.59 (dd, 1H, J=9.0 Hz, J=2.4 Hz), 6.58 (s, 1H), 5.17 (s, 2H, CH$_2$O), 5.14 (s, 2H, CH$_2$O), 4.30 (ddd, 1H, J=10.8 Hz, J=4.2 Hz, J=1.5 Hz), 3.96 (t, 1H, J=10.8 Hz), 3.47 (s, 6H, CH$_3$O), 3.17 (m, 1H, CH), 2.93 (d, 2H, J=8.7 Hz, CH$_2$).

$^{13}$C NMR (75 Mhz, CDCl3, δ): 156.653 (C7), 156.265 (C9), 154.938 (C4'), 134.681 (C10), 130.151 (C8), 128.330 (C6), 116.576 (C3'), 115.532 (C1'), 109.020 (C5), 104.344 (C2'), 94.571 (OCH$_2$O), 94.498 (OCH$_2$O), 71.022 (C2), 55.950 (CH$_3$O), 55.918 (CH$_3$O), 37.893 (C3), 31.891 (C4).

Example 6

Deprotecting the bis-MOM-S-equol to S-Equol ((S)-3-(4-hydroxyphenyl)-chroman-7-ol)

A solution of 42.17 g (0.128 mol) of (S)-bis-MOM-equol in 200 mL of 1:1 mixture of CH$_2$Cl$_2$/MeOH was placed in a 1 L 3-neck round bottom flask equipped with a magnetic stirrer, thermocouple, cooling ice bath and nitrogen line. A total of 200 mL of 10 wt % solution of HCl in MeOH (0.438 mol, 3.4 eq.) was slowly added to pre-chilled (4.8° C.) solution of bis-MOM-equol. The reaction mixture was allowed to warm up to room temperature and monitored by TLC until all starting material is converted to S-equol ($R_f$=0.58 for bis-MOM-equol, 0.28 for mono-MOM-equol, and 0.10 for S-equol in ethyl acetate/hexane=2:8). After 6 hours at room temperature a complete deprotection was observed. Solvent was removed under reduced pressure and precipitated solid was treated with a 500 mL of ice-cold water, extracted with ethyl acetate (2×400 mL) and combined organic phases were washed with diluted sodium bicarbonate (400 mL). Organic layer was dried over sodium sulfate and solvent volume was reduced to about 100 mL. The obtained yellowish solution was carefully diluted with 400 mL of hexane and resulted clear solution was chilled on an ice bath while stirring. Precipitated white solid was filtered off, washed with hexane (3×200 mL) and dried in a vacuum oven overnight to yield 25.24 g of s-equol as a white solid. An additional 3.54 g of the product was obtained from mother liquor. A total 28.78 g (93% isolated yield) of S-equol was obtained as a white solid with mp 162° C. Chemical HPLC and optical purity for synthesized S-equol were found to be 96.69% and 100% ee correspondingly.

Reversed Phase HPLC used to determine chemical purity:
Column: Waters Symmetry C18, 3.5 micron particles, 4.6×75 mm
Mobile phase A: 0.1% TFA in water
Mobile phase B: 0.1% TFA in acetonitrile
Gradient: 5% B to 100% B in 16 minutes, return to initial conditions at 16 minutes.
Detector wavelength=280 nm
Injection volume=5 microliters
Retention time: 7.87 min
HPLC purity: 96.69%
  Optical purity was determine by chiral HPLC:
Column: Chiracel OJ, 4.6×250 mm
Isocratic, 75% (0.2% phosphoric acid in water), 25% acetonitrile
Flow: 0.75 ml/min
Detector wavelength: 215 nm
Retention time: 54.28 min
Chiral purity: 100% ee
Optical rotation: [α]=−19.1° C.

A reported optical rotation for S-equol crystallized from aqueous ethanol is [α]=−21.5° C. (The Merck Index, 1996, 12$^{th}$ edition, p 618).

LC-MS traces and spectra of the S-Equol product are shown in FIGS. 6A and 6B, respectively.

$^1$H NMR and $^{13}$C NMR data appear below.

$^1$H NMR (300 MHz, CDCl$_3$, δ): 9.32 (s, 1H, OH), 9.21 (s, 1H, OH), 7.09 (d, 2H, J=8.4 Hz), 6.86 (d, 1H, J=8.1 Hz), 6.72 (d, 2H, J=8.7 Hz), 6.30 (dd, 1H, J=8.4 J=2.1), 6.21 (d, 1H, J=2.4 Hz), 4.15 (ddd, 1H, CH$_2$O, J=10.5 Hz, J=1.80 Hz), 3.88 (t, 1H, CH$_2$O, J=10.2 Hz), 3.00 (m, 1H, CH), 2.78 (m, 2H, CH$_2$).

$^{13}$C NMR (75 MHz, CDCl$_3$, δ): 156.515 (C7), 156.151 (C4'), 154.557 (C9), 131.711 (C10), 130.134 (C8), 128.346 (C6), 115.321 (C3'), 112.627 (C1'), 108.048 (C5), 102.547 (C2'), 70.309 (C2), 37.197 (C3), 31.324 (C4).

The resulting S-equol product was then converted into the TMS derivate and the TBDMS derivative according to the methods described in the Methods section, in order to improve volatility of the S-equol compound during the mass spec analyses. The GC-MS traces and spectra of the TMS-derivative S-equol products are shown in FIGS. 9A and 9B, respectively. The GC-MS traces and spectra of the TBDMS-derivative S-equol products are shown in FIGS. 9C and 9D, respectively.

Example 7

Enantioselective hydrogenation of bis-MOM dehydro-equol to MOM-protected R-equol ((R)-7-(methoxymethoxy)-3-(4-methoxymethoxy)-phenyl chroman)

A solution of 14.02 g (42.69 mmol) of bis-MOM-dehydroequol and 0.650 g (0.378 mmol, 0.88 mol %) of ((4S,5S)-(−)-O-[1-Benzyl-1-(5-methyl-2-phenyl-4,5-dihydro-oxazol-4-yl)-2-phenylethyl]-diphenylphosphinite-(1,5-COD)-iridium(I)tetrakis-(3,5-bis-trifluoromethyl)-phenylborate (purchased from Strem) in 300 mL of dichloromethane was placed in a 2 L glass reactor equipped with a magnetic stirrer, thermocouple, gas inlet tube and a pressure relief valve. The air was replaced with nitrogen followed by hydrogen purge, and a 60 psig hydrogen pressure was maintained. The reaction mixture was monitored with TLC ($R_f$=0.26 for starting bis-MOM-dehydroequol, greenish spot with PMA on hot plate, and $R_f$=0.28 for bis-MOM-equol, a purple spot with PMA, in ethyl acetate/hexane=1:9). The reaction was kept at 60 psig hydrogen pressure and room temperature for 35 min until all starting material is consumed. Hydrogen was immediately replaced with nitrogen and clear red solution was quenched as quickly as possible with a cold ammonium chloride solution (30 g of NH$_4$Cl, 50 g ice in 300 mL of water). The organics were extracted with dichloromethane (2×200 mL), combined organic phases were washed with 300 mL of water and dried over sodium sulfate. Solvent was removed on rotavap and a red oil was purified on silica gel plug (400 g of SiO2) using ethyl acetate/hexane=2:8 (2 L) and 3:7 (1.5 L) mixtures as an eluent to give a 14.00 g (99.2% yield) of a yellowish oil which slowly crystallized to an off-white solid with mp 37-38° C. This material was used without any purification in the next step.

Figure 7C:
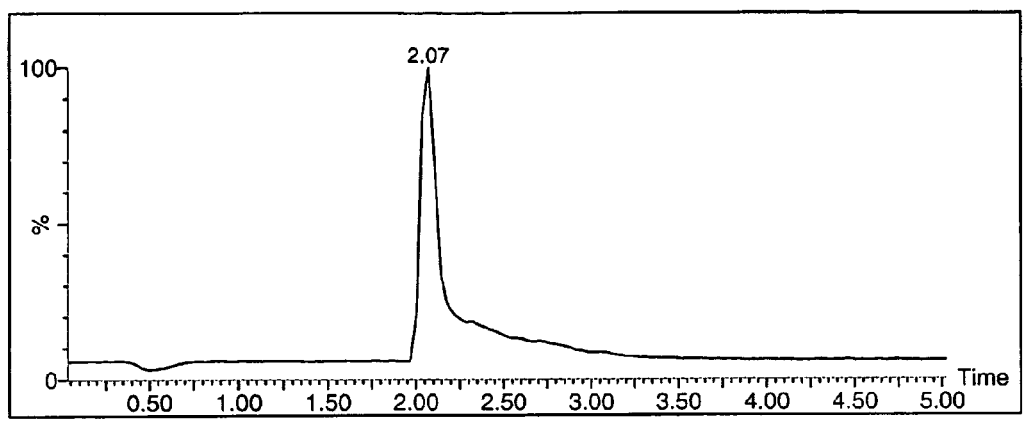
Figure 7D:
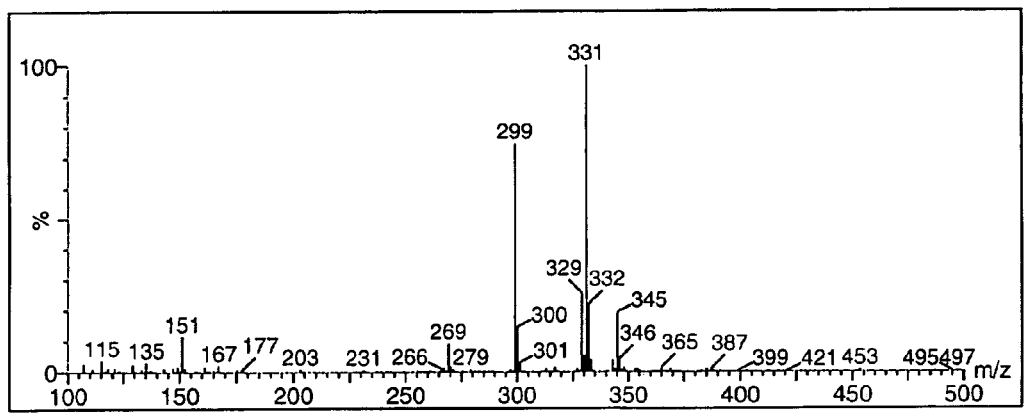

GC-MS traces and spectra of the product are MOM-protected R-equol shown in FIGS. 7A and 7B, respectively. LC-MS traces and spectra of the MOM-protected R-equol product are shown in FIGS. 7C and 7D, respectively.

The $^1$H NMR (300 MHz, CDCl$_3$, δ) and $^{13}$C NMR (75 MHz, CDCl3, δ) were similar to bis-MOM-S-equol.

Example 8

Deprotecting the bis-MOM-R-Equol to R-Equol ((R)-3-(4-hydroxyphenyl)-chroman-7-ol)

A solution of 14.0 g (42.37 mmol) of (R)-bis-MOM-equol in 70 mL of 1:1 mixture of CH$_2$Cl$_2$/MeOH was placed in a 0.5 L 3-neck round bottom flask equipped with a magnetic stirrer, thermocouple, cooling ice bath and nitrogen line. A total of 80 mL of 10 wt % solution of HCl in MeOH (175.3 mmol, 4.1 eq.) was slowly added to pre-chilled (6.3° C.) solution of bis-MOM-equol. The reaction mixture was allowed to warm up to room temperature and monitored by TLC until all starting material is converted to R-equol ($R_f$=0.58 for bis-MOM-equol, 0.28 for mono-MOM-equol, and 0.10 for R-equol in ethyl acetate/hexane=2:8). After 6 hours at room temperature a complete deprotection was observed. Solvent was removed under reduced pressure and precipitated solid (28.3 g) was treated with 325 mL of ice-cold water, extracted with ethyl acetate (2×200 mL). Combined organic phases were washed with diluted sodium bicarbonate (10 g NaHCO$_3$ in 200 mL of water). Organic layer was dried over sodium sulfate and solvent was removed on rotavap to yield 12.5 g of an off-white solid. This solid was passed through silica gel layer (200 g of silica) using EtOAc/hexane=3:7 mixture (3 L) as an eluent. A solvent volume was reduced up to about 100 mL, and 10 g of charcoal was added. The resulted mixture stirred for 10 min, charcoal was filtered off, and hexane was added to the filtrate causing precipitation of the product. The precipitated material was filtered off, washed with hexane (2×50 mL) and dried in a vacuum oven to yield 4.25 g (41% yield) of R-equol as a white solid with mp 163° C. No attempt was made to recover an additional amount of R-equol from mother liquor. Chemical and optical purity were determined using the same methods described for S-equol and were found to be 98.31% (retention time 7.82 min) and 98.6% ee (retention time 57.82 min).

Figure 8A:
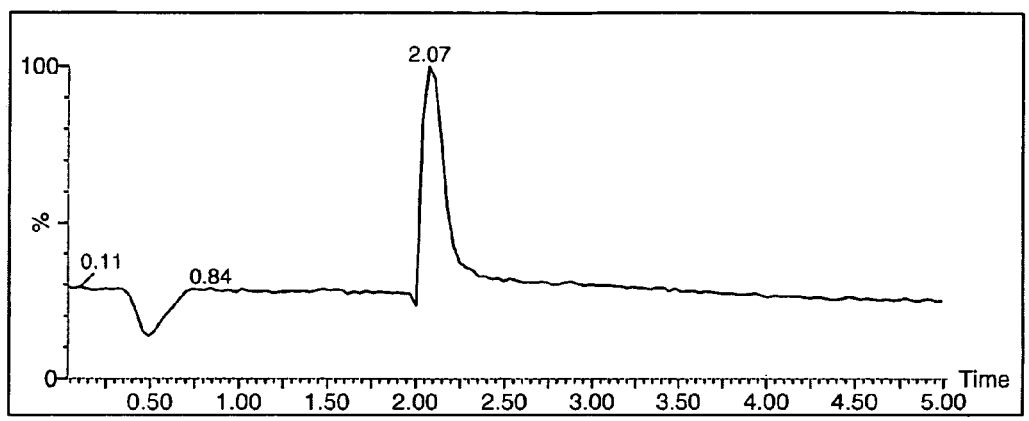
FIGS. 8A and 8B show the LC-MS trace and spectra, respectively, on a R-equol product in accordance with the present invention.
Figure 8B:
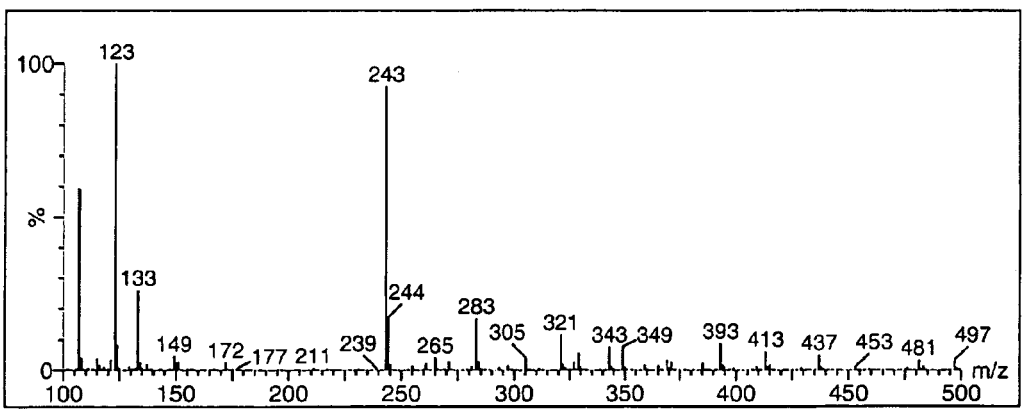

LC-MS traces and spectra of the S-Equol product are shown in FIGS. 8A and 8B, respectively.

The $^1$H NMR (300 MHz, CDCl$_3$, δ) and $^{13}$C NMR (75 MHz, CDCl3, δ) were similar to S-equol.

The resulting R-equol product was then converted into the TMS derivate and the TBDMS derivative according to the methods described in the Methods section, in order to improve volatility of the R-equol compound during the mass spec analyses. The GC-MS traces and spectra of the TMS-derivative R-equol products are shown in FIGS. 10A and 10B, respectively. The GC-MS traces and spectra of the TBDMS-derivative R-equol products are shown in FIGS. 10C and 10D, respectively.

Example 9

Synthesis of 2,3-dehydroequol intermediate product 60 g bis-MOM 3,4-dehydroequol was hydrogenated to enantioselective equol in accordance with Example 6, using 1 mol % of the iridium catalyst and 60 psig hydrogen pressure. During the hydrogenation, the reaction mixture was periodically sampled and analyzed by GC-MS (HP 5890 and MS 5972, with column DB-5 MS, 30 m length, 0.25 mm OD, 0.25 micrometer film, He carrier gas, and flow rate 1.7 mL/min. The temperature was programmed as follows: 50 C for 1 min., raising the temperature by 20 C/min to 300 C, and then held at 300 C for 5 min. Total run time is 18.5 min. Retention time in the GC-MS is 15.77 min. for the equol product, and 16.41 min. for the starting material dehydroequol.

During the run time, an intermediate product peak was observed by GC-MS, distinct from the starting material 3,4-dehydroequol and the product S-equol. The intermediate product had the same molecular weight (MW) as the starting material. A reasonable assumption of a synthesis route leads to the conclusion that the intermediate material is 2,3-dehydroequol. The following mass ratios in the sample and the determined molecular weights are presented below in Table 1 for the starting material (3,4-dehydroequol), the intermediate material (2,3-dehydroequol), and the finished product (S-equol).

TABLE 1

| | | Weight ratio | | |
|---|---|---|---|---|
| | | 3,4 dehydroequol | 2,3 dehydroequol | S-equol |
| | | | MW: | |
| | Time: | 328 | 328 | 330 |
| Mass ratio: | 0 | 100 | 0 | 0 |
| | 20 | 45 | 16 | 38 |
| | 60 | 6 | 0.6 | 93 |
| | 110 | 0 | 0 | 100* |

*including trace product decomposition material

Example 10

Deprotection of bis-MOM 3,4-dehydroequol [3-(4-Hydroxyphenyl)-2H-chromene-7-ol]

A solution 0.42 g (1.28 mmol) of 7-methoxymethoxy-3-(4-methoxymethoxy-phenyl)-2H-chromen (bis-MOM-dehydroequol) in 20 mL of dichloromethane was mixed with 8 mL of 10% HCl/MeOH (17.3 mmol, 13.5 eq.) at 0° C. The resulting solution was kept at this temperature for two days and the reaction was monitored by TLC until all starting material disappeared (R$_f$=0.65 for bis-MOM-dehydroequol and R$_f$=0.14 for dehydroequol in EtOAc/hexane=3:7). The reaction mixture was concentrated on rotavap, the residue diluted with ethyl acetate (50 mL) and quenched with saturated sodium bicarbonate (200 mL). The organic layer was separated, and the aqueous phase was extracted with ethyl acetate (2×100 mL). The organic layers were combined, washed with brine (50 mL), dried over sodium sulfate and concentrated in vacuum to give 0.32 g (104% yield) of pink solid. This solid was dissolved in a minimum amount of ethyl acetate and purified on silica gel plug using ethyl acetate/hexane=1:2 and 1:1.5 mixture as an eluent. Fractions containing dehydroequol were collected and concentrated to give a white solid. The isolated solid was dissolved in ethyl acetate (about 15 mL), filtered and hexane (about 15 mL) was carefully added to the solution resulting in crystallization. The precipitated solid was filtered, washed with hexane (2×20 mL) and dried under nitrogen to give 0.139 g (45% yield) of dehydroequol as a white solid with a faint pink tinge. The second crop (80 mg) was recovered from the filtrate to give a total of 0.219 g (71% isolated yield) of dehydroequol product (7-hydroxy-3-(4-hydroxyphenyl)-2H-chromene).

$^1$H NMR (300 MHz, DMSO-d$_6$, δ): 5.02 (s, 2H, CH$_2$), 6.25 (bs, 1H, C═C—H), 6.33 (dd, 1H, J=1.8 Hz, J=8.4 Hz, ArH), 6.75 (s, 1H, ArH), 6.77 (d, 2H, J=8.7 Hz, ArH), 6.93 (d, 1H, J=7.8 Hz, ArH), 7.33 (d, 2H, J=8.4 Hz, ArH), 9.58 (bs, 2H, OH).

$^{13}$C NMR (75 MHz, DMSO-d$_6$, δ): 66.264, 102.296, 108.525, 114.739, 115.426, 116.688, 125.587, 127.124, 127.254, 127.448, 153.691, 157.016, 158.019.

The invention claimed is:
1. A method for preparing enantioselectively S-equol comprising the steps of:
   a) providing a chromene selected from:

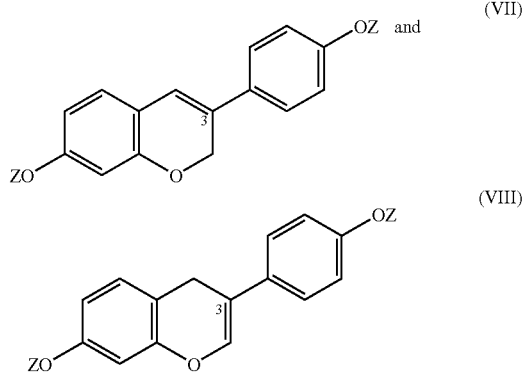

wherein Z is H or PG, and PG is a hydroxy protecting group; and
   b) hydrogenating the chromene in the presence of a metal complex comprising ((4R,5R)-(−)-O-[1-Benzyl-1-(5-methyl-2-phenyl-4,5-dihydro-oxazol-4-yl)-2-phenylethyl]-diphenylphosphinite-(1,5-COD) to form S-equol.

2. The method according to claim 1, wherein the step of hydrogenating is conducted at about 0-150 psig, at a temperature of about 5° C. to about room temperature, and with a solvent selected from dialkyl dihalide solvent.

3. The method according to claim 1, wherein the concentration of the metal complex comprising ((4R,5R)-(−)-O-[1-Benzyl-1-(5-methyl-2-phenyl-4,5-dihydro-oxazol-4-yl)-2-phenylethyl]-diphenylphosphinite-(1,5-COD) is about 0.1 to 5 mol % relative to the chromene.

4. The method according to claim 1, wherein the chromene that is protected is made by dehydrating a chroman-ol compound.

5. The method according to claim 4, wherein the chromal-ol is made by reducing a chroman-one or a chromen-one.

6. The method according to claim 1, wherein the metal is selected from the group consisting of Ru, Rh, Ir, Cu, Ag, Au, Ni, Co, Pd and Pt.

7. The method according to claim 1, wherein the metal is selected from the group consisting of Ru, Rh and Ir.

8. The method according to claim 1, wherein the metal is Ir.

9. A method of preparing enantioselectively S-equol comprising the steps of:
   1) reducing a 3-phenyl-chromen-4-one to a 3-phenyl-chroman-4-one;
   2) reducing the 3-phenyl-chroman-4-one to a 3-phenyl-chroman-4-ol;
   3) dehydrating the 3-phenyl-chroman-4-ol to a 3-phenyl-chromene selected from 3-phenyl-3,4 chromene and 3-phenyl-2,3 chromene; and
   4) hydrogenating the 3-phenyl-chromene in the presence of a metal complex comprising ((4R,5R)-(−)-O-[1-Benzyl-1-(5-methyl-2-phenyl-4,5-dihydro-oxazol-4-yl)-2-phenylethyl]-diphenylphosphinite-(1,5-COD) to form S-equol.

10. The method according to claim 9, wherein the 3-phenyl-chromen-4-one is selected from the group consisting of daidzein and formonenetin and mixtures thereof.

11. The method according to claim 9, wherein the metal is selected from the group consisting of Ru, Rh, Ir, Cu, Ag, Au, Ni, Co, Pd and Pt.

12. The method according to claim 9, wherein the metal is selected from the group consisting of Ru, Rh and Ir.

13. The method according to claim 9, wherein the metal is Ir.

14. A method for preparing enantioselectively R-equol comprising the steps of:
   a) providing a chromene selected from:

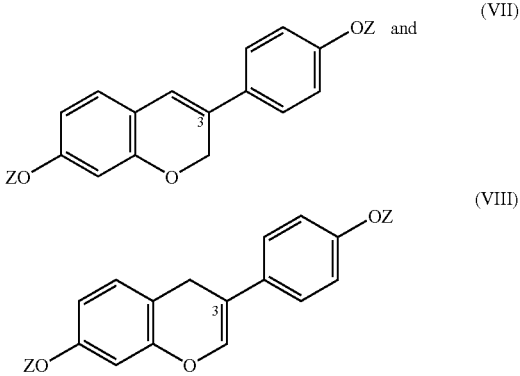

wherein Z is H or PG, and PG is a hydroxy protecting group; and
   b) hydrogenating the chromene in the presence of a metal complex comprising ((4S,5S)-(−)-O-[1-Benzyl-1-(5-methyl-2-phenyl-4,5-dihydro-oxazol4-yl)-2-phenylethyl]-diphenylphosphinite-(1,5-COD) to form R-equol.

15. The method according to claim 14, wherein the step of hydrogenating is conducted at about 0-150 psig, at a temperature of about 5° C. to about room temperature, and with a solvent selected from dialkyl dihalide solvent.

16. The method according to claim 14, wherein the concentration of the metal complex comprising ((4S,5S)-(−)-O-[1-Benzyl-1-(5-methyl-2-phenyl-4,5-dihydro-oxazol4-yl)-2-phenylethyl]-diphenylphosphinite-(1,5-COD) is about 0.1 to 5 mol % relative to the chromene.

17. The method according to claim 14, wherein the chromene that is protected is made by dehydrating a chroman-ol compound.

18. The method according to claim 17, wherein the chromal-ol is made by reducing a chroman-one or a chromen-one.

19. The method according to claim 14, wherein the metal is selected from the group consisting of Ru, Rh, Ir, Cu, Ag, Au, Ni, Co, Pd and Pt.

20. The method according to claim 14, wherein the metal is selected from the group consisting of Ru, Rh and Ir.

21. The method according to claim 14, wherein the metal is Ir.

22. A method of preparing enantioselectively R-equol comprising the steps of:
   1) reducing a 3-phenyl-chromen-4-one to a 3-phenyl-chroman-4-one;
   2) reducing the 3-phenyl-chroman-4-one to a 3-phenyl-chroman-4-ol;
   3) dehydrating the 3-phenyl-chroman-4-ol to a 3-phenyl-chromene selected from 3-phenyl-3,4 chromene and 3-phenyl-2,3 chromene; and
   4) hydrogenating the 3-phenyl-chromene in the presence of a metal complex comprising ((4S,5S)-(−)-O-[1-Benzyl-1-(5-methyl-2-phenyl-4,5-dihydro-oxazol4-yl)-2-phenylethyl]-diphenylphosphinite-(1,5-COD) to form R-equol.

23. The method according to claim 13, wherein the 3-phenyl-chromen-4-one is selected from the group consisting of daidzein and formonenetin and mixtures thereof.

24. The method according to claim 22, wherein the metal is selected from the group consisting of Ru, Rh, Ir, Cu, Ag, Au, Ni, Co, Pd and Pt.

25. The method according to claim 22, wherein the metal is selected from the group consisting of Ru, Rh and Ir.

26. The method according to claim 22, wherein the metal is Ir.

27. The method according to claim 1, wherein the metal complex is ((4R,5R)-(−)-O-[1-Benzyl-1-(5-methyl-2-phenyl-4,5-dihydro-oxazol-4-yl)-2-phenylethyl]-diphenylphosphinite-(1,5-COD)-iridium(I)tetrakis-(3,5-bis-tri-fluoromethyl)-phenylborate.

28. The method according to claim 9, wherein the metal complex is ((4R,5R)-(−)-O-[1-Benzyl-1-(5-methyl-2-phenyl-4,5-dihydro-oxazol-4-yl)-2-phenylethyl]-diphenylphosphinite-(1,5-COD)-iridium(I)tetrakis-(3,5-bis-tri-fluoromethyl)-phenylborate.

29. The method according to claim 14, wherein the metal complex is ((4R,5R)-(−)-O-[1-Benzyl-1-(5-methyl-2-phenyl-4,5-dihydro-oxazol-4-yl)-2-phenylethyl]-diphenylphosphinite-(1,5-COD)-iridium(I)tetrakis-(3,5-bis-tri-fluoromethyl)-phenylborate.

30. The method according to claim 22, wherein the metal complex is ((4R,5R)-(−)-O-[1-Benzyl-1-(5-methyl-2-phenyl-4,5-dihydro-oxazol-4-yl)-2-phenylethyl]-diphenylphosphinite-(1,5-COD)-iridium(I)tetrakis-(3,5-bis-tri-fluoromethyl)-phenylborate.

31. A method for preparing enantioselectively S-equol comprising the steps of:
a) providing a chromene selected from:

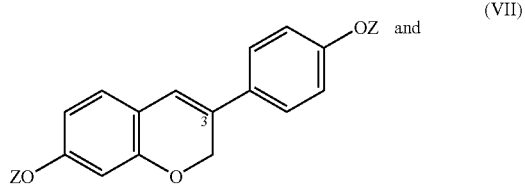
(VII)

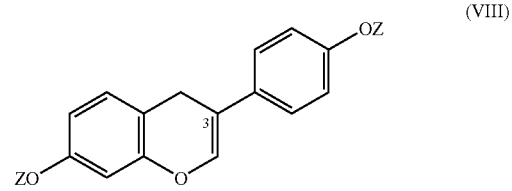
(VIII)

wherein Z is H or PG, and PG is a hydroxy protecting group; and
b) hydrogenating the chromene in the presence of ((4R,5R)-(−)-O-[1-Benzyl-1-(5-methyl-2-phenyl-4,5-dihydro-oxazol-4-yl)-2-phenylethyl]-diphenylphosphinite-(1,5-COD)-iridium(I)tetrakis-(3,5-bis-trifluoromethyl)-phenylborate to form a S-equol.

32. A method of preparing enantioselectively S-equol comprising the steps of:
1) reducing a 3-phenyl-chromen-4-one to a 3-phenyl-chroman-4-one;
2) reducing the 3-phenyl-chroman-4-one to a 3-phenyl-chroman-4-ol;
3) dehydrating the 3-phenyl-chroman-4-ol to a 3-phenyl-chromene selected from 3-phenyl-3,4 chromene and 3-phenyl-2,3 chromene; and
4) hydrogenating the 3-phenyl-chromene in the presence of ((4R,5R)-(−)-O-[1-Benzyl-1-(5-methyl-2-phenyl-4,5-dihydro-oxazol-4-yl)-2-phenylethyl]-diphenylphosphinite-(1,5-COD)-iridium(I)tetrakis-(3,5-bis-tri-fluoromethyl)-phenylborate to form S-equol.

33. A method for preparing enantioselectively R-equol comprising the steps of:
a) providing a chromene selected from:

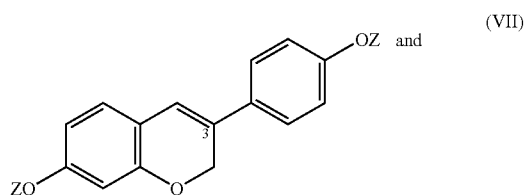
(VII)

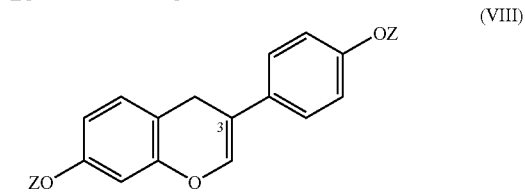
(VIII)

wherein Z is H or PG, and PG is a hydroxy protecting group; and
b) hydrogenating the chromene in the presence of ((4S,5S)-(−)-O-[1-Benzyl-1-(5-methyl-2-phenyl-4,5-dihydro-oxazol4-yl)-2-phenylethyl]-diphenylphosphinite-(1,5-COD)-iridium(I)tetrakis-(3,5-bis-trifluoromethyl)-phenylborate to form R-equol.

34. A method of preparing enantioselectively R-equol comprising the steps of:
1) reducing a 3-phenyl-chromen-4-one to a 3-phenyl-chroman-4-one;
2) reducing the 3-phenyl-chroman-4-one to a 3-phenyl-chroman-4-ol;
3) dehydrating the 3-phenyl-chroman-4-ol to a 3-phenyl-chromene selected from 3-phenyl-3,4 chromene and 3-phenyl-2,3 chromene; and
4) hydrogenating the 3-phenyl-chromene in the presence of ((4S,5S)-(−)-O-[1-Benzyl-1-(5-methyl-2-phenyl-4,5-dihydro-oxazol4-yl)-2-phenylethyl]-diphenylphosphinite-(1,5-COD)-iridium(I)tetrakis-(3,5-bis-trifluoromethyl)-phenylborate to form R-equol.

* * * * *

UNITED STATES PATENT AND TRADEMARK OFFICE
CERTIFICATE OF CORRECTION

| | | |
|---|---|---|
| PATENT NO. | : 7,960,573 B2 | Page 1 of 1 |
| APPLICATION NO. | : 12/435033 | |
| DATED | : June 14, 2011 | |
| INVENTOR(S) | : Kenneth David Reginald Setchell et al. | |

It is certified that error appears in the above-identified patent and that said Letters Patent is hereby corrected as shown below:

In the Specifications

Col. 1, line 44:   replace "(+)" with -- (±) --

Col. 1, line 52:   replace "(+)" with -- (±) --

Col. 2, line 21:   replace "R2" with -- $R^2$ --

Col. 3, line 15:   replace "form" with -- from --

Col. 5, line 43:   replace "R3" with -- $R^3$ --

Col. 7, line 58:   replace "at al." with -- et al. --

Col. 12, line 32:  replace "diohenyl" with -- diphenyl --

Col. 20, line 36:  replace "SiO2" with -- $SiO_2$ --

Col. 20, line 47:  replace "CDCl3" with -- $CDCl_3$ --

Col. 21, line 26:  replace "CDCl3" with -- $CDCl_3$ --

Col. 21, line 51:  replace "50 C" with -- 50 °C --

Col. 21, line 52:  replace "20 C" with -- 20 °C --

Col. 21, line 52:  replace "300 C" with -- 300 °C --

Col. 21, line 53:  replace "300 C" with -- 300 °C --

Signed and Sealed this
Twenty-eighth Day of May, 2013

Teresa Stanek Rea
*Acting Director of the United States Patent and Trademark Office*